United States Patent
Aghaibeik-Lavasani et al.

(10) Patent No.: US 10,632,159 B2
(45) Date of Patent: Apr. 28, 2020

(54) COMPOSITION AND METHOD FOR TREATMENT AND PROPHYLAXIS OF INTESTINAL INFECTION AND INFLAMMATION

(71) Applicant: IMMUNEBIOTECH MEDICAL SWEDEN AB, Lund (SE)

(72) Inventors: Shahram Aghaibeik-Lavasani, Lund (SE); Mehrnaz Nouri, Lund (SE)

(73) Assignee: IMMUNEBIOTECH MEDICAL SWEDEN AB, Lund (SE)

(*) Notice: Subject to any disclaimer, the term of this patent is extended or adjusted under 35 U.S.C. 154(b) by 0 days.

(21) Appl. No.: 15/753,692

(22) PCT Filed: Aug. 23, 2016

(86) PCT No.: PCT/SE2016/050787
§ 371 (c)(1),
(2) Date: Feb. 20, 2018

(87) PCT Pub. No.: WO2017/034460
PCT Pub. Date: Mar. 2, 2017

(65) Prior Publication Data
US 2018/0243353 A1 Aug. 30, 2018

(30) Foreign Application Priority Data
Aug. 25, 2015 (SE) ...................... 1551099

(51) Int. Cl.
A61K 35/747 (2015.01)
C12R 1/25 (2006.01)
C12R 1/24 (2006.01)
C12N 1/20 (2006.01)
C12R 1/225 (2006.01)
A61P 31/04 (2006.01)
A61P 1/00 (2006.01)

(52) U.S. Cl.
CPC .............. *A61K 35/747* (2013.01); *A61P 1/00* (2018.01); *A61P 31/04* (2018.01); *C12N 1/20* (2013.01); *C12R 1/225* (2013.01); *C12R 1/24* (2013.01); *C12R 1/25* (2013.01); *Y02A 50/473* (2018.01); *Y02A 50/481* (2018.01)

(58) Field of Classification Search
CPC ........ A61K 35/747; C12N 1/20; C12R 1/225; C12R 1/25; C12R 1/24
See application file for complete search history.

(56) References Cited

U.S. PATENT DOCUMENTS

2008/0311097 A1* 12/2008 Israelsen .............. A61K 31/685
424/93.44
2012/0315249 A1* 12/2012 Olmstead ............... A61K 45/06
424/93.3

FOREIGN PATENT DOCUMENTS

WO WO-03010298 A1 2/2003
WO WO-2009047537 A 4/2009
WO WO-2012142605 A1 * 10/2012 ............. A61K 35/74

OTHER PUBLICATIONS

Sleator et al., "Designer Probiotics: A Potential Therapeutic for Clostridium Difficile?", Journal of Medical Microbiology, vol. 57, pp. 793-794, 2008.
Iannitti et al., "Therapeutical Use of Probiotic Formulations in Clinical Practice", Clinical Nutrition, vol. 29, pp. 701-725, 2010.
Tejero-Sarinena et al., "Antipathogenic Activity of Probiotics Against *Salmonella typhimurium* and Clostridium Difficile in Anaerobic Batch Culture Systems: Is it Due to Synergies in Probiotic Mixtures or The Specificity of Single Strains?", Anaerobe, vol. 24, pp. 60-65, 2013.
Hell et al., "Probiotics in Clostridium Difficile Infection", Beneficial Microbes, vol. 4, Issue 1, pp. 39-51, 2013.
Kondepubi et al., "A Novel Multi-Strain Probiotic and Synbiotic Supplement for Prevention of Clostridium Difficile Infection in a Murine Model", Microbiol Immunolog, vol. 58, pp. 552-558, 2014.
Aazami et al., "Characterization of Some Potentially Probiotic Lactobacillus Strains Isolated from Iranian Native Chickens", The Journal of General and Applied Microbiology, vol. 60, pp. 215-221, 2014.
International Search Report dated Jan. 3, 2017 for PCT Application No. PCT/SE2016/050787.

* cited by examiner

*Primary Examiner* — Ruth A Davis
(74) *Attorney, Agent, or Firm* — Moser Taboada

(57) ABSTRACT

The present invention relates to a composition for use in the treatment and/or prevention of a gastrointestinal condition, comprising at least one *Lactobacillus* strain, wherein the *Lactobacillus* strain is chosen from the group consisting of one *L. salivarius* strain, three *L. plantarum* strains and one *L. brevis* strain, wherein the *L. salivarius* strain is *L. salivarius* CW30 (LMG P-28887), wherein the *L. plantarum* strains are *L. plantarum* Y1An734 (LMG P-28886), *L. plantarum* SH1313 (LMG P-28884), and *L. plantarum* KS1 1 (LMG P-28885), and wherein the *L. brevis* strain is *L. brevis* SH1 1 1 (LMG P-28888). The present invention also relates to an enema comprising a composition according to the present invention. The present invention also relates to an isolated strain chosen from the group *L. salivarius* CW30 (LMG P-28887), *L. plantarum* Y1An734 (LMG P-28886), *L. plantarum* SH1313 (LMG P-28884), *L. plantarum* KS11 (LMG P-28885) and *L. brevis* SH111 (LMG P-28888). The present invention also relates to an isolated strain of *L. salivarius* CW30 (LMG P-28887) for use in the treatment and/or prevention of an infection by *Clostridium difficile* NAP/027.

14 Claims, 28 Drawing Sheets

Figure 1:
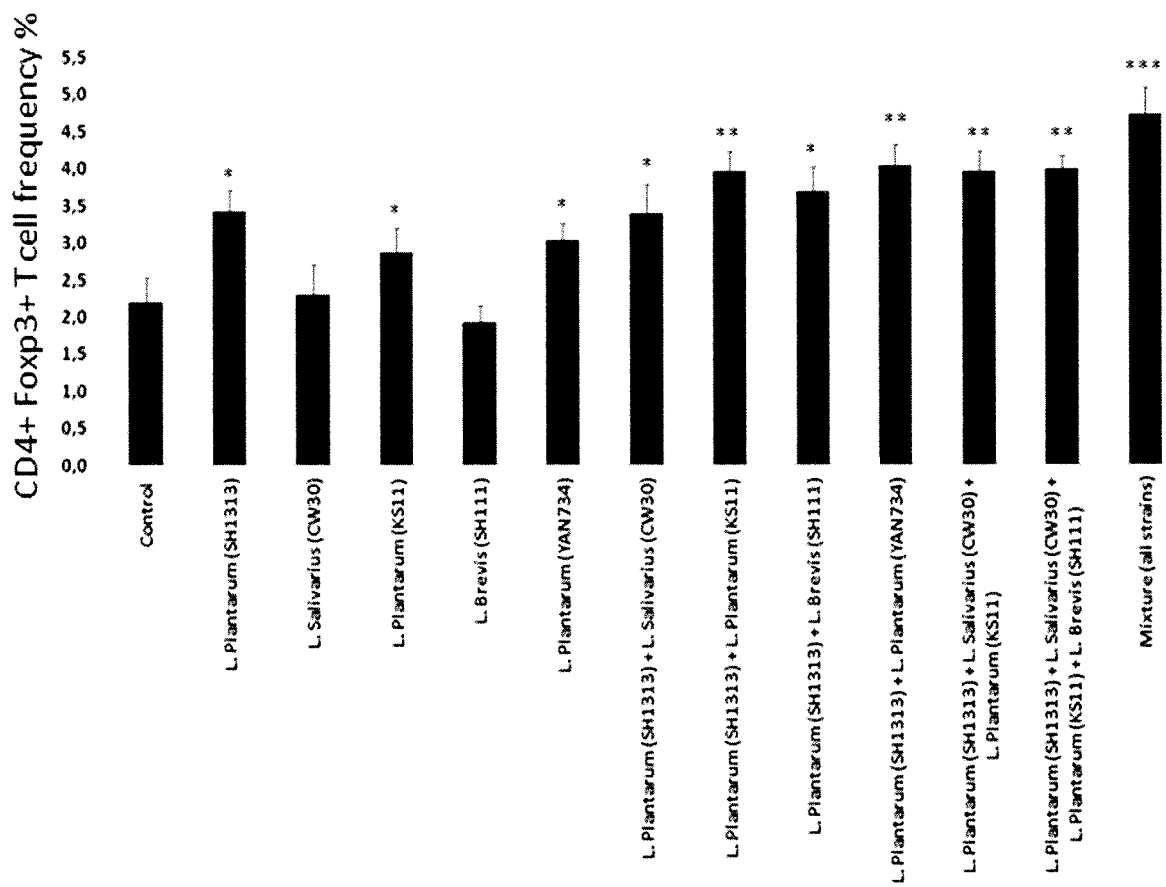

Figure 3:

Table 1

| Strain number: | C. difficile ||||||||||||||||||| NAP1/027 ||
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 1 | 2 |
| L. Plantarum | - | + | - | - | - | - | - | - | - | - | - | - | - | - | - | - | - | - | - | - | - |
| L. Plantarum | - | - | - | - | - | - | - | - | - | - | - | - | - | - | - | - | - | - | - | - | - |
| L. Plantarum (SH1313) | + | + | + | - | + | - | + | - | + | + | - | - | + | + | - | + | + | + | + | - | - |
| L. Brevis | + | + | - | - | - | - | - | - | - | + | - | - | - | - | - | - | - | - | - | - | - |
| L. Salivarius (CW30) | - | + | - | + | + | - | - | + | + | + | - | - | + | + | + | - | + | - | + | + | + |
| L. Paracasei | - | + | - | - | - | - | - | - | - | - | - | - | - | - | - | - | - | - | - | - | - |
| L. Vaginalis | - | - | - | - | - | - | - | - | - | - | - | - | - | - | - | - | - | - | - | - | - |
| L. Reuteri | - | + | - | - | - | - | + | - | - | - | - | - | - | - | - | - | - | - | - | - | - |
| L. Plantarum | - | - | - | - | - | - | - | - | - | - | - | - | - | - | - | - | - | - | - | - | - |
| L. Brevis (SH111) | + | + | - | - | - | - | - | - | + | + | + | + | + | - | - | + | + | + | - | + | + |
| L. Plantarum | - | + | - | - | - | - | - | + | - | - | - | - | - | - | - | - | - | - | - | - | - |
| L. Plantarum | - | + | - | - | - | - | - | - | - | - | - | - | - | - | - | - | - | - | - | - | - |
| L. Plantarum | - | - | - | - | - | + | - | - | - | - | - | - | - | - | - | - | - | + | - | - | - |
| L. Salivarius | - | + | - | - | - | + | - | - | - | + | - | - | - | - | - | - | - | - | + | - | - |
| L. Plantarum (KS11) | + | + | + | - | + | + | - | - | + | + | - | + | + | + | + | - | + | + | - | - | - |
| L. Brevis | - | + | - | - | - | - | - | - | - | + | + | - | - | - | - | - | - | - | + | - | - |
| L. Casei | - | + | - | - | - | - | - | - | - | - | - | - | - | - | - | - | - | - | - | - | - |
| L. Plantarum (YAN734) | - | - | - | + | - | - | - | + | - | + | - | + | - | + | - | - | - | + | + | - | - |
| Mixture of SH313+CW30+SH111+KS11+YAN734 | + | + | + | + | + | + | + | + | + | + | + | + | + | + | + | + | + | + | + | + | + |

Figure 4:

Table 2

| | L. Plantarum (SH1313) | L. Salivarius (CW30) | L. Brevis (SH111) | L. Plantarum (KS11) | L. Plantarum (YAN734) |
|---|---|---|---|---|---|
| L. Plantarum (SH1313) | | | | | - |
| L. Salivarius (CW30) | - | | + | | - |
| L. Brevis (SH111) | - | + | | + | + |
| L. Plantarum (KS11) | - | - | + | | - |
| L. Plantarum (YAN734) | - | + | - | - | |

Figure 5:

Table 3

| | L. Plantarum (SH1313) | L. Salivarius (CW30) | L. Brevis (SH111) | L. Plantarum (KS11) | L. Plantarum (YAN734) |
|---|---|---|---|---|---|
| Erythromycin | S | S | S | S | S |
| Vancomycin | R | R | R | R | R |
| Metronidazole | R | R | R | R | R |

Figure 7:

Table 4

| | Salmonella enteritidis | Salmonella typhimurium | Escherichia coli |
|---|---|---|---|
| Mixture of L. Plantarum (SH1313) + L. Salivarius (CW30) + L. Brevis (SH111) + L. Plantarum (KS11) + L. Plantarum (YAN734) | ++++ | +++ | ++++ |

Figure 8:

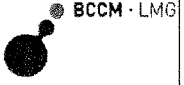

| | RECEIPT IN THE CASE OF AN ORIGINAL DEPOSIT ISSUED PURSUANT TO RULE 7.1, BY BCCM/LMG<br>BCCM/LMG/BP/4 | F418C |
|---|---|---|
| BCCM · LMG | | 14/04/2014 |
| | | Page 1 of 2 |

BUDAPEST TREATY ON THE INTERNATIONAL RECOGNITION OF THE DEPOSIT OF MICRO-ORGANISMS FOR THE PURPOSES OF PATENT PROCEDURE

| The depositor<br><br>Name or institution*: Lund University<br><br>*In case the depositor is a legal entity, the authorised representing person according to BCCM/LMG/BP/1 is:<br>    Name:    Dr. Shahram Aghaibeik-Lavasani<br>    Function:<br><br>Address:    Department of Biology<br>              Sölvegatan 35, Building C<br>              SE-223 62 Lund, SWEDEN | International form<br>BCCM/LMG/BP/4/<br>15-403<br><br>(number to be filled in by IDA) |
|---|---|

I. IDENTIFICATION OF THE MICRO-ORGANISM

| Identification reference given by the depositor:<br>Lacto 4 | Accession number given by the International Depositary Authority: LMG P-28887 |
|---|---|

II. SCIENTIFIC DESCRIPTION AND/OR PROPOSED TAXONOMIC DESIGNATION

The micro-organism identified under section I above was accompanied by:

☐ a scientific description;

☒ a proposed taxonomic designation.

III. RECEIPT AND ACCEPTANCE

This International Depositary Authority accepts the micro-organism identified under section I above, which was received by it on (date of the original deposit): May 19, 2015

IV. RECEIPT OF REQUEST FOR CONVERSION (IF APPLICABLE)

Figure 8:

The micro-organism identified under section I above was received by this International Depositary Authority on (date of the original deposit):
and a request to convert the original deposit to a deposit under the Budapest Treaty was received by it on (date of receipt of request for conversion):

Figure 8 cont:

Figure 8 cont:

| 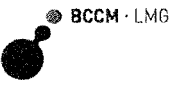 BCCM · LMG | VIABILITY STATEMENT ISSUED PURSUANT TO RULE 10.2. BY BCCM/LMG BCCM/LMG/BP/9 | F423C |
|---|---|---|
| | | 14/04/2014 |
| | | Page 1 of 2 |

BUDAPEST TREATY ON THE INTERNATIONAL RECOGNITION OF THE DEPOSIT OF
MICRO-ORGANISMS FOR THE PURPOSES OF PATENT PROCEDURE

| Party to whom the viability statement is issued (as mentioned in form BP1)<br><br>Name: Dr. Shahram Aghaibeik-Lavasani<br>Address: Lund University, Department of Biology<br>Sölvegatan 35, Building C<br>SE-223 62 Lund, SWEDEN | International form<br>BCCM/LMG/BP/9/<br>15-403<br><br>(number to be filled in by IDA) |
|---|---|

| I. DEPOSITOR |
|---|
| Name or institution*: Lund University<br><br>*In case the depositor is a legal entity, the authorised representing person according to BCCM/LMG/BP/1 is:<br>Name: Dr. Shahram Aghaibeik-Lavasani<br>Function.<br><br>Address: Department of Biology<br>Sölvegatan 35, Building C<br>SE-223 62 Lund, SWEDEN |
| II. IDENTIFICATION OF THE MICRO-ORGANISM |

| Accession number given by the International Depositary Authority: LMG P-28887 | Date of the original deposit (or where applicable: date of a new deposit or date of receipt of request for conversion): May 19, 2015 |
|---|---|

| III. VIABILITY STATEMENT |
|---|
| The viability of the micro-organism identified under section II above was tested on May 19-21, 2015 (Give date. In the cases referred to in Rule 10.2.(a)(ii) and (iii), refer to the most recent viability test).<br><br>On that date, the said micro-organism was<br>☒ viable.<br>☐ no longer viable. |

Figure 9:

| ![BCCM·LMG] | RECEIPT IN THE CASE OF AN ORIGINAL DEPOSIT ISSUED PURSUANT TO RULE 7.1. BY BCCM/LMG<br>BCCM/LMG/BP/4 | F418C |
|---|---|---|
| | | 14/04/2014 |
| | | Page 1 of 2 |

BUDAPEST TREATY ON THE INTERNATIONAL RECOGNITION OF THE DEPOSIT OF MICRO-ORGANISMS FOR THE PURPOSES OF PATENT PROCEDURE

| The depositor<br><br>Name or institution*: Lund University<br><br>*In case the depositor is a legal entity, the authorised representing person according to BCCM/LMG/BP/1 is:<br>  Name.   Dr. Shahram Aghaibeik-Lavasani<br>  Function:<br><br>Address:   Department of Biology<br>           Sölvegatan 35, Building C<br>           SE-223 62 Lund, SWEDEN | International form<br>BCCM/LMG/BP/4/<br>15-404<br><br>(number to be filled in by IDA) |
|---|---|

| I. IDENTIFICATION OF THE MICRO-ORGANISM | |
|---|---|
| Identification reference given by the depositor:<br>Lacto 5 | Accession number given by the International Depositary Authority: LMG P-28888 |

| II. SCIENTIFIC DESCRIPTION AND/OR PROPOSED TAXONOMIC DESIGNATION |
|---|
| The micro-organism identified under section I above was accompanied by:<br><br>☐ a scientific description;<br><br>☒ a proposed taxonomic designation. |

| III. RECEIPT AND ACCEPTANCE |
|---|
| This International Depositary Authority accepts the micro-organism identified under section I above, which was received by it on (date of the original deposit) May 19, 2015 |

| IV. RECEIPT OF REQUEST FOR CONVERSION (IF APPLICABLE) |
|---|
| The micro-organism identified under section I above was received by this International Depositary Authority on (date of the original deposit):<br>and a request to convert the original deposit to a deposit under the Budapest Treaty was received by it on (date of receipt of request for conversion): |

Figure 9:

Figure 9 cont:

Figure 9 cont:

|  BCCM·LMG | VIABILITY STATEMENT ISSUED PURSUANT TO RULE 10.2. BY BCCM/LMG<br>BCCM/LMG/BP/9 | F423C |
|---|---|---|
| | | 14/04/2014 |
| | | Page 1 of 2 |

BUDAPEST TREATY ON THE INTERNATIONAL RECOGNITION OF THE DEPOSIT OF MICRO-ORGANISMS FOR THE PURPOSES OF PATENT PROCEDURE

| Party to whom the viability statement is issued (as mentioned in form BP1)<br><br>Name: Dr. Shahram Aghaibeik-Lavasani<br>Address: Lund University, Department of Biology<br>Sölvegatan 35, Building C<br>SE-223 62 Lund, SWEDEN | International form<br>BCCM/LMG/BP/9/<br>15-404<br><br>(number to be filled in by IDA) |
|---|---|

| I. DEPOSITOR | |
|---|---|
| Name or institution*: Lund University<br><br>*In case the depositor is a legal entity, the authorised representing person according to BCCM/LMG/BP/1 is:<br>Name: Dr. Shahram Aghaibeik-Lavasani<br>Function.<br><br>Address: Department of Biology<br>Sölvegatan 35, Building C<br>SE-223 62 Lund, SWEDEN | |
| II. IDENTIFICATION OF THE MICRO-ORGANISM | |
| Accession number given by the International Depositary Authority: LMG P-28888 | Date of the original deposit (or where applicable: date of a new deposit or date of receipt of request for conversion): May 19, 2015 |
| III. VIABILITY STATEMENT | |
| The viability of the micro-organism identified under section II above was tested on May 19-21, 2015 (Give date. In the cases referred to in Rule 10.2.(a)(ii) and (iii), refer to the most recent viability test).<br><br>On that date, the said micro-organism was<br>☒ viable.<br>☐ no longer viable. | |

Figure 10:

| ![BCCM·LMG] | RECEIPT IN THE CASE OF AN ORIGINAL DEPOSIT ISSUED PURSUANT TO RULE 7.1. BY BCCM/LMG | F418C |
|---|---|---|
| | | 14/04/2014 |
| | BCCM/LMG/BP/4 | Page 1 of 2 |

BUDAPEST TREATY ON THE INTERNATIONAL RECOGNITION OF THE DEPOSIT OF MICRO-ORGANISMS FOR THE PURPOSES OF PATENT PROCEDURE

| The depositor<br><br>Name or institution*: Lund University<br><br>*In case the depositor is a legal entity, the authorised representing person according to BCCM/LMG/BP/1 is:<br>    Name:    Dr. Shahram Aghaibeik-Lavasani<br>    Function:<br><br>Address:    Department of Biology<br>              Sölvegatan 35, Building C<br>              SE-223 62 Lund, SWEDEN | International form<br>BCCM/LMG/BP/4/<br>15-400<br><br>(number to be filled in by IDA) |
|---|---|

| I. IDENTIFICATION OF THE MICRO-ORGANISM ||
|---|---|
| Identification reference given by the depositor:<br>Lacto 1 | Accession number given by the International Depositary Authority: LMG P-28884 |

| II. SCIENTIFIC DESCRIPTION AND/OR PROPOSED TAXONOMIC DESIGNATION |
|---|
| The micro-organism identified under section I above was accompanied by:<br><br>☐ a scientific description;<br>☒ a proposed taxonomic designation. |

| III. RECEIPT AND ACCEPTANCE |
|---|
| This International Depositary Authority accepts the micro-organism identified under section I above, which was received by it on (date of the original deposit): May 19, 2015 |

| IV. RECEIPT OF REQUEST FOR CONVERSION (IF APPLICABLE) |
|---|
| The micro-organism identified under section I above was received by this International Depositary Authority on (date of the original deposit):<br>and a request to convert the original deposit to a deposit under the Budapest Treaty was received by it on (date of receipt of request for conversion): |

Figure 10:
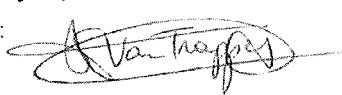

Figure 10 cont:
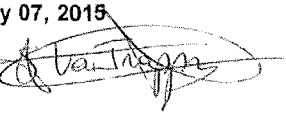

Figure 10 cont:

| ![BCCM-LMG] | VIABILITY STATEMENT ISSUED PURSUANT TO RULE 10.2. BY BCCM/LMG BCCM/LMG/BP/9 | F423C |
| | | 14/04/2014 |
| | | Page 1 of 2 |

BUDAPEST TREATY ON THE INTERNATIONAL RECOGNITION OF THE DEPOSIT OF MICRO-ORGANISMS FOR THE PURPOSES OF PATENT PROCEDURE

| Party to whom the viability statement is issued (as mentioned in form BP1) | International form BCCM/LMG/BP/9/ 15-400 (number to be filled in by IDA) |
|---|---|
| Name: Dr. Shahram Aghaibeik-Lavasani<br>Address: Lund University, Department of Biology<br>Sölvegatan 35, Building C<br>SE-223 62 Lund, SWEDEN | |

| I. DEPOSITOR |
|---|
| Name or institution*: Lund University<br><br>*In case the depositor is a legal entity, the authorised representing person according to BCCM/LMG/BP/1 is:<br>    Name: Dr. Shahram Aghaibeik-Lavasani<br>    Function:<br><br>Address:     Department of Biology<br>             Sölvegatan 35, Building C<br>             SE-223 62 Lund, SWEDEN |

| II. IDENTIFICATION OF THE MICRO-ORGANISM ||
|---|---|
| Accession number given by the International Depositary Authority: LMG P-28884 | Date of the original deposit (or where applicable: date of a new deposit or date of receipt of request for conversion): May 19, 2015 |

| III. VIABILITY STATEMENT |
|---|
| The viability of the micro-organism identified under section II above was tested on May 19-21, 2015 (Give date. In the cases referred to in Rule 10.2.(a)(ii) and (iii), refer to the most recent viability test).<br><br>On that date, the said micro-organism was<br>☒ viable.<br>☐ no longer viable. |

Figure 11:

BUDAPEST TREATY ON THE INTERNATIONAL RECOGNITION OF THE DEPOSIT OF MICRO-ORGANISMS FOR THE PURPOSES OF PATENT PROCEDURE

| The depositor | |
|---|---|
| Name or institution*: Lund University<br><br>*In case the depositor is a legal entity, the authorised representing person according to BCCM/LMG/BP/1 is:<br>  Name: Dr. Shahram Aghaibeik-Lavasani<br>  Function:<br><br>Address:  Department of Biology<br>  Sölvegatan 35, Building C<br>  SE-223 62 Lund, SWEDEN | International form BCCM/LMG/BP/4/ 15-401<br><br>(number to be filled in by IDA) |

| I. IDENTIFICATION OF THE MICRO-ORGANISM | |
|---|---|
| Identification reference given by the depositor:<br>Lacto 2 | Accession number given by the International Depositary Authority: LMG P-28885 |

| II. SCIENTIFIC DESCRIPTION AND/OR PROPOSED TAXONOMIC DESIGNATION |
|---|
| The micro-organism identified under section I above was accompanied by:<br><br>☐ a scientific description;<br>☒ a proposed taxonomic designation. |

| III. RECEIPT AND ACCEPTANCE |
|---|
| This International Depositary Authority accepts the micro-organism identified under section I above, which was received by it on (date of the original deposit): May 19, 2015 |

| IV. RECEIPT OF REQUEST FOR CONVERSION (IF APPLICABLE) |
|---|
| The micro-organism identified under section I above was received by this International Depositary Authority on (date of the original deposit):<br>and a request to convert the original deposit to a deposit under the Budapest Treaty was received by it on (date of receipt of request for conversion): |

Figure 11 cont:

Figure 11 cont:

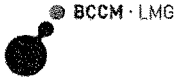

| | VIABILITY STATEMENT ISSUED PURSUANT TO RULE 10.2. BY BCCM/LMG BCCM/LMG/BP/9 | F423C |
|---|---|---|
| | | 14/04/2014 |
| | | Page 1 of 2 |

BUDAPEST TREATY ON THE INTERNATIONAL RECOGNITION OF THE DEPOSIT OF MICRO-ORGANISMS FOR THE PURPOSES OF PATENT PROCEDURE

| Party to whom the viability statement is issued (as mentioned in form BP1)<br><br>Name: Dr. Shahram Aghaibeik-Lavasani<br>Address: Lund University, Department of Biology<br>Sölvegatan 35, Building C<br>SE-223 62 Lund, SWEDEN | International form BCCM/LMG/BP/9/ 15-401<br><br>(number to be filled in by IDA) |
|---|---|

| I. DEPOSITOR |
|---|
| Name or institution*: Lund University<br><br>*In case the depositor is a legal entity, the authorised representing person according to BCCM/LMG/BP/1 is:<br>    Name:    Dr. Shahram Aghaibeik-Lavasani<br>    Function:<br><br>Address:    Department of Biology<br>    Sölvegatan 35, Building C<br>    SE-223 62 Lund, SWEDEN |

| II. IDENTIFICATION OF THE MICRO-ORGANISM ||
|---|---|
| Accession number given by the International Depositary Authority: LMG P-28885 | Date of the original deposit (or where applicable: date of a new deposit or date of receipt of request for conversion): May 19, 2015 |

| III. VIABILITY STATEMENT |
|---|
| The viability of the micro-organism identified under section II above was tested on May 19-21, 2015 (Give date. In the cases referred to in Rule 10.2.(a)(ii) and (iii), refer to the most recent viability test).<br><br>On that date, the said micro-organism was<br>☒ viable.<br>☐ no longer viable. |

Figure 11 cont:

|  BCCM · LMG | VIABILITY STATEMENT ISSUED PURSUANT TO RULE 10.2. BY BCCM/LMG<br>BCCM/LMG/BP/9 | F423C |
|---|---|---|
| | | 14/04/2014 |
| | | Page 2 of 2 |

IV. CONDITIONS UNDER WHICH THE VIABILITY TEST HAS BEEN PERFORMED

(Fill in if the information has been requested and if the results of the test were negative)

V. INTERNATIONAL DEPOSITARY AUTHORITY

Belgian Coordinated Collections of Micro-organisms (BCCM)
Laboratorium voor Microbiologie – Bacteriënverzameling (LMG)
Universiteit Gent
K.L. Ledeganckstraat 35
9000 Gent
Belgium Name: Dr. S. Van Trappen          Date: July 07, 2015
Function: Curator Patent deposit collection     Signature: 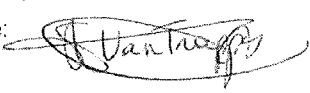

Figure 12:

| BCCM·LMG | RECEIPT IN THE CASE OF AN ORIGINAL DEPOSIT ISSUED PURSUANT TO RULE 7.1. BY BCCM/LMG BCCM/LMG/BP/4 | F418C |
| --- | --- | --- |
| | | 14/04/2014 |
| | | Page 1 of 2 |

BUDAPEST TREATY ON THE INTERNATIONAL RECOGNITION OF THE DEPOSIT OF MICRO-ORGANISMS FOR THE PURPOSES OF PATENT PROCEDURE

| The depositor | |
| --- | --- |
| Name or institution*: Lund University *In case the depositor is a legal entity, the authorised representing person according to BCCM/LMG/BP/1 is: Name: Dr. Shahram Aghaibeik-Lavasani Function: Address: Department of Biology Sölvegatan 35, Building C SE-223 62 Lund, SWEDEN | International form BCCM/LMG/BP/4/ 15-402 (number to be filled in by IDA) |

| I. IDENTIFICATION OF THE MICRO-ORGANISM | |
| --- | --- |
| Identification reference given by the depositor: Lacto 3 | Accession number given by the International Depositary Authority: LMG P-28886 |

| II. SCIENTIFIC DESCRIPTION AND/OR PROPOSED TAXONOMIC DESIGNATION |
| --- |
| The micro-organism identified under section I above was accompanied by: ☐ a scientific description; ☒ a proposed taxonomic designation. |

| III. RECEIPT AND ACCEPTANCE |
| --- |
| This International Depositary Authority accepts the micro-organism identified under section I above, which was received by it on (date of the original deposit): May 19, 2015 |

| IV. RECEIPT OF REQUEST FOR CONVERSION (IF APPLICABLE) |
| --- |
| The micro-organism identified under section I above was received by this International Depositary Authority on (date of the original deposit): and a request to convert the original deposit to a deposit under the Budapest Treaty was received by it on (date of receipt of request for conversion): |

Figure 12 cont:

Figure 12 cont:

|  BCCM · LMG | VIABILITY STATEMENT ISSUED PURSUANT TO RULE 10.2. BY BCCM/LMG BCCM/LMG/BP/9 | F423C |
|---|---|---|
| | | 14/04/2014 |
| | | Page 1 of 2 |

BUDAPEST TREATY ON THE INTERNATIONAL RECOGNITION OF THE DEPOSIT OF MICRO-ORGANISMS FOR THE PURPOSES OF PATENT PROCEDURE

| Party to whom the viability statement is issued (as mentioned in form BP1)<br><br>Name: Dr. Shahram Aghaibeik-Lavasani<br>Address: Lund University, Department of Biology<br>Sölvegatan 35, Building C<br>SE-223 62 Lund, SWEDEN | International form<br>BCCM/LMG/BP/9/<br>15-402<br><br>(number to be filled in by IDA) |
|---|---|

| I. DEPOSITOR |
|---|
| Name or institution*: Lund University<br><br>*In case the depositor is a legal entity, the authorised representing person according to BCCM/LMG/BP/1 is:<br>Name: Dr. Shahram Aghaibeik-Lavasani<br>Function: |
| Address: Department of Biology<br>Sölvegatan 35, Building C<br>SE-223 62 Lund, SWEDEN |
| II. IDENTIFICATION OF THE MICRO-ORGANISM |

| Accession number given by the International Depositary Authority: LMG P-28886 | Date of the original deposit (or where applicable: date of a new deposit or date of receipt of request for conversion): May 19, 2015 |
|---|---|

| III. VIABILITY STATEMENT |
|---|
| The viability of the micro-organism identified under section II above was tested on May 19-21, 2015 (Give date. In the cases referred to in Rule 10.2.(a)(ii) and (iii), refer to the most recent viability test).<br><br>On that date, the said micro-organism was<br>☒ viable.<br>☐ no longer viable. |

Figure 12 cont:
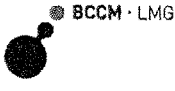

Figure 13:

| Sugar | Time | CW30 | KS11 | Y1An734 | SH1313 | SH111 |
|---|---|---|---|---|---|---|
| Glucose | 24h | 3 | 3 | 3 | 3 | 3 |
| Glucose | 48h | 3 | 3 | 3 | 3 | 3 |
| Glucose | 72h | 3 | 3 | 3 | 3 | 3 |
| Amygdalin | 24h | - | 2 | 2 | 2 | - |
| Amygdalin | 48h | - | 2 | 2 | 2 | - |
| Amygdalin | 72h | - | 2 | 2 | 2 | - |
| Arabinose | 24h | - | - | - | - | - |
| Arabinose | 48h | - | - | - | - | - |
| Arabinose | 72h | - | - | - | - | - |
| Cellobiose | 24h | - | 2 | 3 | 3 | - |
| Cellobiose | 48h | - | 2 | 3 | 3 | - |
| Cellobiose | 72h | - | 2 | 3 | 3 | 1 |
| Esculin | 24h | - | 1 | 1 | 1 | - |
| Esculin | 48h | - | 1 | 1 | 1 | - |
| Esculin | 72h | - | 1 | 1 | 1 | - |
| Galactose | 24h | 3 | 3 | 3 | 3 | - |
| Galactose | 48h | 3 | 3 | 3 | 3 | - |
| Galactose | 72h | 3 | 3 | 3 | 3 | - |
| Gluconate | 24h | - | 1 | 2 | 2 | - |
| Gluconate | 48h | - | 1 | 2 | 1 | - |
| Gluconate | 72h | - | 1 | 1 | 1 | - |
| Lactose | 24h | 3 | 3 | 2 | 2 | - |
| Lactose | 48h | 3 | 3 | 2 | 3 | 1 |
| Lactose | 72h | 3 | 3 | 2 | 3 | 1 |
| Maltose | 24h | 3 | 3 | 2 | 2 | - |
| Maltose | 48h | 3 | 3 | 2 | 3 | - |
| Maltose | 72h | 3 | 3 | 2 | 3 | - |
| Mannitol | 24h | 3 | 3 | 2 | 3 | - |
| Mannitol | 48h | 3 | 3 | 2 | 3 | 1 |
| Mannitol | 72h | 3 | 3 | 2 | 3 | 1 |
| Mannose | 24h | 3 | 3 | 2 | 2 | - |
| Mannose | 48h | 3 | 3 | 2 | 3 | - |
| Mannose | 72h | 3 | 2 | 2 | 3 | 1 |
| Melezitose | 24h | 1 | 3 | 2 | 2 | - |
| Melezitose | 48h | - | 3 | 2 | 3 | - |
| Melezitose | 72h | - | 3 | 2 | 3 | 1 |
| Melibiose | 24h | 2 | 3 | 2 | 2 | - |
| Melibiose | 48h | 2 | 3 | 2 | 3 | - |
| Melibiose | 72h | 3 | 3 | 2 | 3 | - |
| Raffinose | 24h | 2 | - | - | - | - |
| Raffinose | 48h | 2 | - | 2 | 1 | - |
| Raffinose | 72h | 3 | 2 | 3 | 3 | 1 |
| Ribose | 24h | - | 3 | 2 | 2 | 2 |
| Ribose | 48h | - | 3 | 2 | 3 | 1 |
| Ribose | 72h | - | 3 | 2 | 3 | 1 |
| Salicin | 24h | - | - | - | - | - |
| Salicin | 48h | - | - | - | - | - |
| Salicin | 72h | - | - | - | - | - |
| Sorbitol | 24h | 2 | 3 | 3 | 2 | - |
| Sorbitol | 48h | 2 | 3 | 3 | 3 | 1 |
| Sorbitol | 72h | 3 | 2 | 3 | 3 | 1 |
| Sucrose | 24h | 2 | 3 | 3 | 2 | - |
| Sucrose | 48h | 2 | 3 | 3 | 3 | 1 |
| Sucrose | 72h | 3 | 3 | 3 | 3 | 1 |
| Trehalose | 24h | 2 | 3 | 2 | 3 | - |
| Trehalose | 48h | 2 | 3 | 2 | 3 | 1 |
| Trehalose | 72h | 3 | 2 | 2 | 3 | 1 |
| Xylose | 24h | - | - | - | - | 2 |
| Xylose | 48h | - | - | - | - | 2 |
| Xylose | 72h | - | - | - | 1 | 1 |

COMPOSITION AND METHOD FOR TREATMENT AND PROPHYLAXIS OF INTESTINAL INFECTION AND INFLAMMATION

TECHNICAL FIELD OF THE INVENTION

The present invention relates to a composition for use in the treatment and/or prevention of a gastrointestinal condition, comprising at least one *Lactobacillus* strain. Especially, the *Lactobacillus* strain may be a *L. salivarius* strain, a *L. plantarum* strain and/or a *L. brevis* strain and the gastrointestinal condition may be a bacterial infection by *Clostridium difficile, Salmonella* or *Escherichia coli*.

BACKGROUND

The mammalian intestine is colonized by an estimated 100 trillion bacteria, which have co-evolved with the host in a symbiotic relationship. This collection of microbial populations in the host is referred to as the microbiota. The microbiota can efficiently protect the intestine against colonization by exogenous pathogens and potentially harmful indigenous microorganisms (pathobionts). Mucosal immune responses to normal intestinal bacteria are also important for development and physiology of the host. Breakdown in immunological tolerance to microbiota lead to inappropriate local and systemic immune responses to intestinal bacterial communities that may contribute to multiple disease states such as inflammatory bowel disease (IBD) and irritable bowel syndrome (IBS). The increased prevalence of these chronic conditions has been suggested to be influenced by factors including bacterial infections, antibiotic exposure, as well as dietary factors, stress and degree of hygiene.

Alteration in the balance of the intestinal microbiota results in disrupted intestinal homeostasis, which increases the risk of pathogen infection and the overgrowth of pathobionts, particularly in immunocompromised hosts. Pathobionts are typically colitogenic in that they can trigger intestinal inflammation. Pseudomembranous colitis which results in severe diarrhea, fever and abdominal pain, is caused by overgrowth of *Clostridium difficile* (CD), a Gram-positive anaerobic bacterium, following long-term treatment with broad-spectrum antibiotics.

Long-term hospitalization, antibiotic treatment, immune deficiency, cancerous diseases, chemotherapy, and steroid treatment are the main causes of nosocomial diarrhea infections triggered usually by CD but also other enteric bacterial pathogens such as *Salmonella, Shigella, Camphylobacter*, and *Yersinia*.

CD has become one of the most serious causes of antibiotic-associated diarrhea. Conventional treatment includes vancomycin or metronidazole for ten days. However, recurrence (occurs in 10 to 25% of cases) is getting increasingly common and represent the greatest challenge associated with CD infections (CDI).

Increasing rates of CDI have been reported in Canada and the United States, with a larger proportion of severe and recurrent cases than previously reported. In US, the rates of hospital discharges with CDI listed as any diagnosis increased from 3.82 per 1000 discharges in 2000 to 8.75 per 1000 discharges in 2008; increases were especially prominent among those ≥65 years of age. Preliminary data indicate that the number of death certificates with enterocolitis due to CDI increased from 793 in 1999 to 7483 in 2008 in US. The rate of pediatric CDI-related hospitalizations also increased between 1997 and 2006, from 0.724 to 1.28 per 1000 hospitalizations. The highest incidence was reported in children 1-4 years of age. The raised incidence and virulence of CDI have coincided with the spread of the hypervirulent CD referred to as NAP1/027, also known as CD BUNAP1/027 (a restriction endonuclease analysis group BI, pulse-field gel electrophoresis type NAP1, and polymerase chain reaction ribotype 027). NAP1/027 strain produces a binary toxin and up to 16-fold more toxins than most other hospital outbreak associated strains. Subsequently, epidemics of CDI caused by CD NAP1/027 have been recognized in hospitals in European countries, e.g. the United Kingdom, the Netherlands, Belgium, Austria, and Sweden. The major changes in the epidemiology of CDI during recent years, with increases in incidence and severity of disease have made it a global public health challenge.

The only products used to treat CDI are antibiotics, such as metronidazole, vancomycin, and the recently approved Dificid. Although their high clinical cure rates, 15-30% of patients still experience a recurrence, with each recurrence increasing the risk of further infections. Both the appropriate and the inappropriate use of antibiotics are also associated with the rise in resistance to antibiotics, the emergence of vancomycin resistant new biotypes of *Clostridium difficile*, and the increasing incidence of chronic inflammatory conditions.

The rates of severe cases of CDI have increased during the recent years and the hypervirulent CD NAP1/027 has been associated with recent outbreaks throughout the world. European Centre for Disease Prevention and Control (ECDC) found (in 2011) that the prevalence of CD NAP1/027 was 5% in the 34 European countries. Large outbreaks of severe, often fatal, colitis have also been reported in North America and Europe. Such an infection may, as a last option when no other treatment has been effective, be treated by the transplantation of feces from a healthy individual. Such transplantation, in addition to the possible psychological discomfort, may also pose the risk of transplanting potentially harmful microorganisms from the donor. Thus, although fecal microbiota transplant has demonstrated some promising results for treating CDI, physicians are concerned about potential infection risks and long-term safety. Recent reports on an obesity onset followed after a fecal transplantation indicate risks and long-term safety issues. In addition, the cumbersome procedures associated with the technology limit its routine use. There are no standard protocols and procedures regarding donor screening/selection, preparation of fecal materials, sanitation issues, recipient preparation, and route of administration.

Thus, there is a need for more effective therapeutic treatment options as well as preventative treatments for CDI.

An altered composition of microbiota interferes with normal intestinal functions at diverse levels. In addition to triggering the immune system and proinflammatory cytokines, it may also induce release of microbial metabolites, activation of hypothalamic-pituitaryadrenal (HPA) axis with increase of cortisol, leading to alterations of intestinal motility and sensation, disruption of intestinal barrier and impaired production of neurotransmitters with an increased response to stressful events. These complications may cause the IBS which is a chronic functional disorder of the gastrointestinal system and of the most common causes of illness and workplace absenteeism. No cure is available and IBS patients have to rely on treatments to relive symptoms such pain, diarrhea and constipation, associated with side effects. The cause of IBS is unknown but there is increasing evidence showing changes in the composition of luminal and mucosal microbiota among IBS patients compared to healthy individuals. Examples of these modifications are a decreased amount of lactobacilli and bifidobacteria along with an increased amount of *Clostridium* in IBS patients. Investigations of gut microbiota of children diagnosed with IBS also indicates a dysbiosis mainly dominated by *Clostridium*.

Therapeutic interventions using lactobacilli are therefore attractive in IBS. A number of studies have concluded that lactobacilli, in general, benefit patients with IBS but it has been difficult to define relative benefits of different bacterial strains. Weak effects and mixed results are primarily due to lack of proper bacterial strain selection and the often poor quality of the studies.

SUMMARY OF THE INVENTION

The above and other objects of the invention are achieved, in full or at least in part, by a composition comprising at least one *Lactobacillus* strain chosen from the group consisting of one *L. salivarius* strain, three *L. plantarum* strains and one *L. brevis* strain, wherein the *L. salivarius* strain may be *L. salivarius* CW30 (LMG P-28887), the *L. plantarum* strains may be chosen from the group comprising *L. plantarum* SH1313 (LMG P-28884), *L. plantarum* KS11 (LMG P-28885) and *L. plantarum* Y1An734 (LMG P-28886) and the *L. brevis* strain may be *L. brevis* SH111 (LMG P-28888). Preferably, the composition comprises all of *L. salivarius* CW30 (LMG P-28887), *L. plantarum* SH1313 (LMG P-28884), *L. plantarum* KS11 (LMG P-28885), *L. plantarum* Y1An734 (LMG P-28886) and *L. brevis* SH111 (LMG P-28888).

The present document is also directed to a probiotic composition comprising *L. plantarum* Y1An734 (LMG P-28886), *L. plantarum* SH1313 (LMG P-28884), and *L. plantarum* KS11 (LMG P-28885). The present document is also directed to composition comprising *L. salivarius* CW30 (LMG P-28887), *L. plantarum* SH1313 (LMG P-28884), *L. plantarum* KS11 (LMG P-28885), *L. plantarum* Y1An734 (LMG P-28886) and *L. brevis* SH111 (LMG P-28888). The bacteria in the composition may consist of *L. salivarius* CW30 (LMG P-28887), *L. plantarum* SH1313 (LMG P-28884), *L. plantarum* KS11 (LMG P-28885), *L. plantarum* Y1An734 (LMG P-28886) and *L. brevis* SH111 (LMG P-28888) in combination, but the composition may also comprise additional bacterial strains.

The present document is also directed to a probiotic composition comprising a mixture of equal amounts of bacteria of the strains *L. plantarum* Y1An734 (LMG P-28886), *L. plantarum* SH1313 (LMG P-28884), *L. plantarum* KS11 (LMG P-28885), *L. salivarius* CW30 (LMG P-28887) and *L. brevis* SH111 (LMG P-28888). It is to be understood that in the context of the present document by the term "equal" and the like in connection with amount of bacteria it is intended that the number of bacterial cells of the different bacterial strains are present in an amount relative to each other so that no bacterial strain is present in an amount more than 10 times of the other, and preferably less than 9 times, 8 times, 7 times, 6 times, 5 times, 4 times, 3 times or 2 times of the other strains. Preferably, when the bacteria are present in equal amounts, each bacterial strain is present in an amount so that the ratio to each other bacterial strain is about 1:1.

The present document is also directed to a composition for use in the treatment and/or prevention of a gastrointestinal condition, wherein said composition comprises at least one *Lactobacillus* strain, wherein the *Lactobacillus* strain is chosen from the group consisting of one *L. salivarius* strain, three *L. plantarum* strains and one *L. brevis* strain, wherein the *L. salivarius* strain is *L. salivarius* CW30 (LMG P-28887), wherein the *L. plantarum* strains are *L. plantarum* Y1An734 (LMG P-28886), *L. plantarum* SH1313 (LMG P-28884), and *L. plantarum* KS11 (LMG P-28885), and wherein the *L. brevis* strain is *L. brevis* SH111 (LMG P-28888).

The treatment may be a curative treatment, i.e. a treatment which restores the health of the subject. During a curative treatment, the composition may be administered as an enema. When administered as an enema, the composition may be administered a limited number of times, typically between one and five times, during a short period of time, e.g. during the course of one day to five weeks. When administered orally, the composition may be administered daily during e.g. 1 to 6 weeks.

For certain conditions or in certain patients, the treatment may have a more supportive character, where the composition is administered several times over a longer, sometimes lifelong, periods. The composition may be administered with an interval of one day to two weeks.

The composition may also be used as a prophylactic (preventive) treatment, for example during longer periods of intake of antibiotics in order to support and/or preserve and/or restore a healthy bacterial flora of the gastrointestinal tract.

The composition may comprise at least one *L. salivarius* strain, wherein the *L. salivarius* strain may be *L. salivarius* CW30 (LMG P-28887). An advantage of this is that *L. salivarius* CW30 (LMG P-28887) has a potential antimicrobial effect. The present document is therefore also directed to a composition wherein the bacterial part of the composition comprises, or consists of, *L. salivarius* CW30 (LMG P-28887).

Further, the composition may comprise at least *L. salivarius* CW30 (LMG P-28887) and at least one of the strains *L. plantarum* SH1313 (LMG P-28884), *L. plantarum* KS11 (LMG P-28885), *L. plantarum* Y1An734 (LMG P-28886) and *L. brevis* SH111 (LMG P-28888). The present document is therefore also directed to a composition wherein the bacterial part of the composition comprises or consists of *L. salivarius* CW30 (LMG P-28887) and at least one of the strains *L. plantarum* SH1313 (LMG P-28884), *L. plantarum* KS11 (LMG P-28885), *L. plantarum* Y1An734 (LMG P-28886) and *L. brevis* SH111 (LMG P-28888). An advantage of the *L. plantarum* strains *L. plantarum* Y1An734 (LMG P-28886), *L. plantarum* SH1313 (LMG P-28884), *L. plantarum* KS11 (LMG P-28885) is that these strains possess anti-inflammatory properties. In addition, these strains may prevent and/or treat intestinal inflammation and improve the gut barrier function. Furthermore, these *L. plantarum* strains may act in synergy with *L. salivarius* CW30 (LMG P-28887) and *L. brevis* SH111 (LMG P-28888) in inhibitory activity against a broader range of pathogenic bacteria associated with gastrointestinal complications. This results in the therapeutic correction of dysbiosis of the gut microbiota promoting to restore the homeostasis of the immune system. An advantage of *L. brevis* SH111 (LMG P-28888) is that it has a synergistic antibacterial potential. This strain has been demonstrated to have a broad antimicrobial activity against different Gram-positive pathogenic bacteria, such as *Staphylococcus aureus* and Gram-negative, such as *Escherichia coli*.

The composition may alternatively comprise at least *L. plantarum* Y1An734 (LMG P-28886), *L. plantarum* SH1313 (LMG P-28884), and *L. plantarum* KS11 (LMG P-28885). The present document is therefore also directed to a composition wherein the bacterial part of the composition comprises or consists of *L. plantarum* Y1An734 (LMG P-28886), *L. plantarum* SH1313 (LMG P-28884), and *L. plantarum* KS11 (LMG P-28885). This composition may further comprise *L. salivarius* CW30 (LMG P-28887) and *L. brevis* SH111 (LMG P-28888).

The gastrointestinal condition may be a diarrhoea, antibiotic-associated diarrhoea (AAD), gastroenteritis, acute gastroenteritis and/or infectious diarrhoea.

Furthermore, the gastrointestinal condition may be a bacterial infection by *Clostridium difficile*, *Salmonella* and/or *Escherichia coli*. The gastrointestinal condition may also be caused by a diarrhoeal disease due to bacteria such as *Campylobacter jejuni*, *Salmonella typhimurium*, *Yersinia enterocolitica*, enteropathogenic *E. coli* (EPEC), enterohemorrhagic *E. coli* (EHEC), *Shigella* spp., *Staphylococcus aureus*, *Listeria monocytogenes*, *Vibrio cholera*, *Vibrio parahaemolyticus* and *Bacillus cereus*. The gastrointestinal condition may also be due to a viral infection, such as Rotavirus associated diarrhoea. The gastrointestinal condition may also be post infective diarrhoea.

Especially, the gastrointestinal condition may be an infection by *Clostridium difficile* NAP1/027. One advantage of the present invention is that it quickly resolves the disease by targeting the pathogenic bacteria and to re-establishing immunological tolerance and intestinal homeostasis. A second advantage is that the use of purified *Lactobacillus* strains with well-defined beneficial health effects avoids the use of feces or other compositions that involve critical safety and health issues.

The gastrointestinal condition may be irritable bowel syndrome (IBS) or inflammatory bowel disease (IBD). The term inflammatory bowel disease (IBD) includes, among other conditions, Crohn's disease and ulcerative colitis.

The gastrointestinal condition may also be pouchitis or post infection colitis.

The composition may be administered orally, such as in a beverage or food product. The composition may be administered as a beverage, in which case the *Lactobacillus* strain(s) are suspended in a liquid. The liquid may e.g. be water, milk, a salt-sugar solution or a gruel. Alternatively, the composition may be administered as a porridge or pudding. The composition may be included in a pill, which can be swallowed by the patient. An advantage of these routes of administration is that they do not require any advanced medical equipment. Another advantage of administering the composition as a beverage, porridge, pudding or pill is that the patient can control when the beverage, porridge, pudding or pill is swallowed.

The composition may be administered as an enema. An advantage of this route of administration is that it can be performed using equipment which is commonly used in hospitals. An advantage of this route of administration is that the composition may be administered at the location in the gastrointestinal tract where it is most effective. Another advantage is that it is performed by healthcare professionals; the patients can content with a few treatments and will be assessed regularly by care providers.

The composition may be administered as an infusion into the upper gastrointestinal tract. The composition may be administered through a medical device, such as a nasoduodenal tube. An advantage of this route of administration is that it can be performed using equipment which is commonly used in hospitals. Another advantage of this route of administration is that the composition may be administered at the location in the gastrointestinal tract where it is most effective. Another advantage is that the bacterial composition bypasses the stomach and its acidic environment and are directly infused to the intestine.

The composition may be administered through a medical device, such as a nasogastric tube. The composition may be administered via colonoscopy.

The total amount of *Lactobacillus* may be $10^9$ to $10^{13}$ CFU per treatment, e.g. $10^9$, $10^{10}$, $10^{11}$, $10^{12}$ or $10^{13}$ CFU per treatment. In the case of nasoduodenal infusion the treatment may be repeated after one day, a few days or a week for at least two times.

The composition may be freeze-dried. An advantage of this is that the bacteria may be preserved for long-term storage and no advanced storage facilities are needed to handle the bacteria.

The freeze-dried composition may be contained in a bag, a jar, a capsule or any other kind of container such as a pill. The freeze-dried composition may be one of several components in a mixture. Further, the freeze-dried composition may also be one of several components of a pill. Other conventional additives may naturally be added to the freeze-dried compositions or to any of the other mentioned compositions as disclosed herein in order to provide stable compositions with suitable shelf life. A skilled person would know such conventional additives and the amount to be used in the compositions.

The composition may further comprise a fiber component.

The fiber component may be chosen from the group consisting of oat fiber, wheat fiber, rye fiber, chia fiber, corn fiber, barley fiber, potato fiber, fruit fiber, vegetable fiber, cereal fiber and fiber from algae.

Other examples of suitable fibers include different kinds of soluble and insoluble fibers. For example, fibers originating from seeds (e.g linseeds and psyllium seeds) or from nuts (such as walnuts, coconuts, almonds) may be used. Dietary fibers such as inulin may be used. Other conventional additives may be added to the fiber containing compositions.

The bacteria may be suspended in a gruel, a pap, a porridge or a pudding.

The gruel may be oat gruel. Other gruels which may be used include wheat gruel, barley gruel, rye gruel or corn or maize gruel.

Before administration of the composition according to the present invention, the fresh or freeze-dried bacterial composition may be suspended in a suitable liquid. The liquid may be a pharmaceutically acceptable liquid component or any type of suitable medium, e.g. one of the media described above. Preferably, distilled water or buffered aqueous media are used, which contain pharmaceutically acceptable salts and buffers. Suitable salt solutions are PBS (Phosphate-buffered saline), GBSS (Gey's Balanced Salt Solution), EBSS (Earle's balanced salt solution), HBSS (Hank's Balanced Salt Solution), and SBF (Synthetic/Simulated Body Fluid). The liquid component can also be of a more hydrophobic nature depending of the application.

In the case of oral administration, different flavourings may be added in order to make the mixture comprising the composition more pleasant to taste.

The composition may be ready to use after reactivation in the suitable medium for 24 h at room temperature or up to one week at 4° C. However, it should be noted that the time period and temperature may vary depending on i.e. the medium used.

The composition may further compromise one or more therapeutic agents, such as an agent against the bacterial induced infection and/or the inflammatory condition.

The composition may comprise the above mentioned five strains or even more, as long as at least one of the above mentioned bacterial strains are present.

A composition as described above may be comprised in an enema. An advantage of such an enema is that the route of administration can be performed using equipment which is commonly used in hospitals. Another advantage of this route of administration is that the composition may be administered at the location in the gastrointestinal tract where it is most effective, i.e. in the colon.

The volume of composition administered will vary depending on the age and size of the person receiving the enema. However general guidelines would be: Infant: 250 ml or less, School-aged child: 200-500 ml, Adult: 200-1,000 ml.

The composition may be a pharmaceutical formulation.

The present document also provides an isolated strain chosen from the group consisting of L. salivarius CW30 (LMG P-28887), L. plantarum SH1313 (LMG P-28884), L. plantarum KS11 (LMG P-28885), L. plantarum Y1An734 (LMG P-28886) and L. brevis (LMG P-28888). The bacterial strains are biologically pure.

The present document is also provides an isolated strain of L. salivarius for use in the treatment and/or prevention of an infection by Clostridium difficile NAP1/027, wherein the strain is L. salivarius CW30 (LMG P-28887).

The present document is also directed to a method for the treatment and/or prevention of a gastrointestinal condition said method comprising the step of administering a pharmaceutically effective amount of a composition comprising one or more of a bacterial strain selected from the group consisting of L. salivarius CW30 (LMG P-28887), L. plantarum SH1313 (LMG P-28884), L. plantarum KS11 (LMG P-28885), L. plantarum Y1An734 (LMG P-28886) and L. brevis (LMG P-28888), an enema comprising one or more of these bacteria, or one or more of an isolated bacterial strain selected from the group consisting of L. salivarius CW30 (LMG P-28887), L. plantarum SH1313 (LMG P-28884), L. plantarum KS11 (LMG P-28885), L. plantarum Y1An734 (LMG P-28886) and L. brevis (LMG P-28888), to a subject in need thereof. Said gastrointestinal is a gastrointestinal condition as disclosed elsewhere herein.

Use of a composition comprising one or more of a bacterial strain selected from the group consisting of L. salivarius CW30 (LMG P-28887), L. plantarum SH1313 (LMG P-28884), L. plantarum KS11 (LMG P-28885), L. plantarum Y1An734 (LMG P-28886) and L. brevis (LMG P-28888), an enema comprising one or more of these bacteria, or one or more of an isolated bacterial strain selected from the group consisting of L. salivarius CW30 (LMG P-28887), L. plantarum SH1313 (LMG P-28884), L. plantarum KS11 (LMG P-28885), L. plantarum Y1An734 (LMG P-28886) and L. brevis (LMG P-28888) for the preparation of a medicament for the treatment and/or prevention of a gastrointestinal condition. Said gastrointestinal is a gastrointestinal condition as disclosed elsewhere herein.

Other objectives, features and advantages of the present invention will appear from the following detailed disclosure, from the attached claims, as well as from the figures. It is noted that the invention relates to all possible combination of features.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

As used herein, the term "comprising" and variations of that term are not intended to exclude other additives, components, integers or steps.

Definition of Strains

All strains were deposited at BCCM/LMG (Belgian Coordinated Collections of Micro-organisms/Laboratorium voor Microbiologie, Universiteit Gent (UGent)), Gent, Belgium on May 19, 2015. The depositor is Lund University, as represented by Shahram Aghaibeik-Lavasani, Department of Biology, Sölvegatan 35, Building C, 223 62 Lund, Sweden.

The deposition numbers are as follows.

| | |
|---|---|
| L. plantarum SH1313 | LMG P-28884 |
| L. plantarum KS11 | LMG P-28885 |
| L. plantarum Y1An734 | LMG P-28886 |
| L. salivarius CW30 | LMG P-28887 |
| L. brevis SH111 | LMG P-28888 |

The strains are biologically pure.
Definition of Strains and Terms
CFU=colony forming units

DESCRIPTION OF THE TABLES AND FIGURE

FIG. 1 shows the percentage of $CD4^+Foxp3^+$ T cells after co-incubation of lactobacilli with freshly isolated immune cells from murine intestinal lymphoid tissues. $1\times10^6$ immune cells were incubated with either single Lactobacillus sp. or in combination with two or several. * represents a p-value≤0.05,  a p-value≤0.01 and * a pvalue≤0.001 in comparison with the control.

Figure 2:
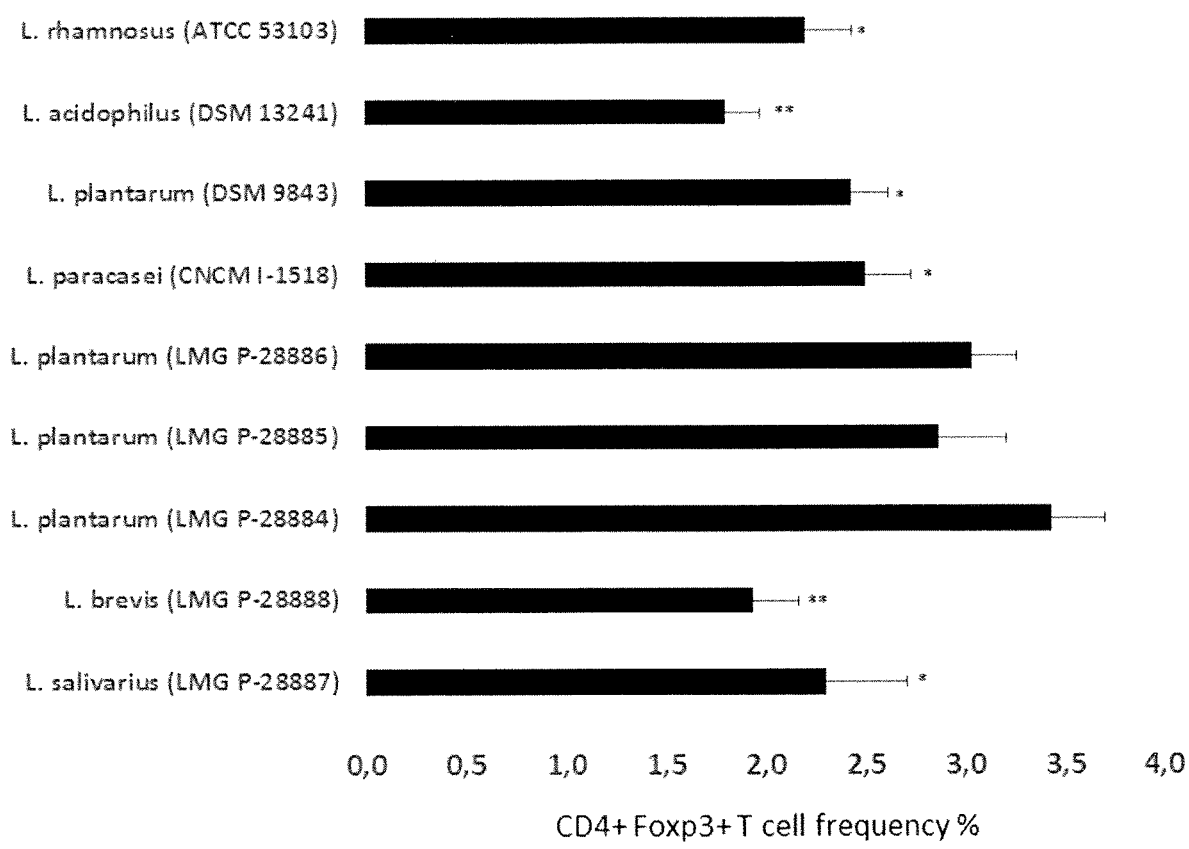

FIG. 2 shows the percentage of $CD4^+Foxp3^+$ T cells after co-incubation of lactobacilli with immune cells from murine intestinal lymphoid tissues as described above. $1\times10^6$ immune cells were incubated with single Lactobacillus species including five lactobacilli strains LMG P-28884-P28888 and four lactobacilli strains isolated from different commercially available food products (L. paracasei CNCM I-1518, L. plantarum DSM 9843, L. acidophilus DSM 13241 and L. rhamnosus ATCC 53103). * represents a p-value≤0.05,  a p-value≤0.01 and * a pvalue≤0.001 in comparison with the L. plantarum SH1313 (LMG P-28884).

FIG. 3 Table 1 shows the antagonistic activity of different species of lactobacilli against Clostridium difficile including hyper-virulent NAP1/027 strains; − indicating no inhibition, + indicating inhibition, or no growth around the lactobacilli streaks.

FIG. 4 Table 2 shows a cross-streak method to investigate the inter-species inhibition of five different Lactobacillus strains. For each group, the strains at the top of the table were the (first-streaked) tester strain; − indicating no inhibition, + indicating inhibition, or no growth in the zone where the Lactobacillus streaks converged.

FIG. 5 Table 3 shows the antibiotic susceptibility test of Lactobacillus strains.

Figure 6:
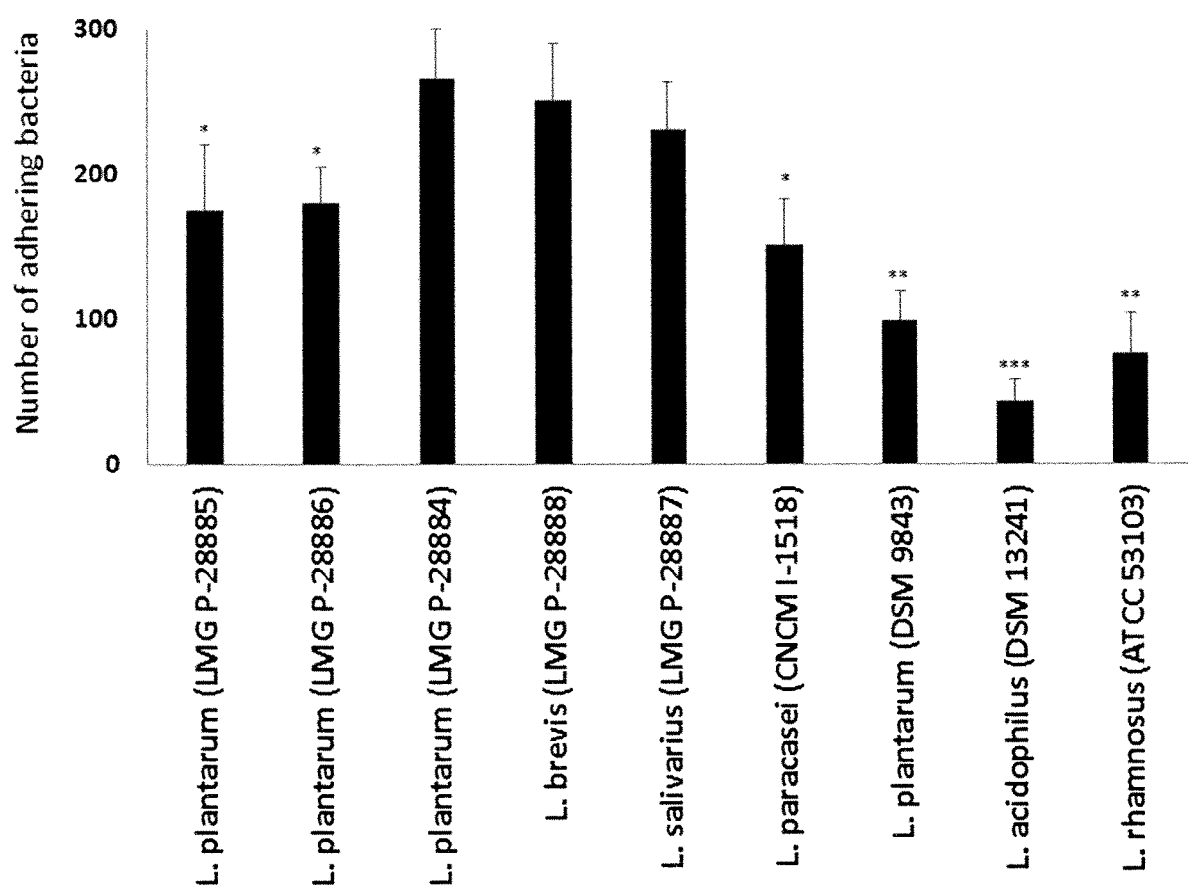

FIG. 6 shows the ability of lactobacilli strains to adhere to the human epithelial colorectal cells. Lactobacillus species including the five lactobacilli strains LMG P-28884-P28888 and four lactobacilli strains isolated from different commercially available food products (L. paracasei CNCM I-1518, L. plantarum DSM 9843, L. acidophilus DSM 13241 and L. rhamnosus ATCC 53103) were used for comparison. An equal number of cells for each strain (5×10⁸), was independently incubated (1 h at 37° C.) with a monolayer of fully differentiated Caco-2 cells. The cells were washed and stained with Giemsa stain solution. The adherent bacteria in randomly selected microscopic fields were counted and averaged. * represents a p-value≤0.05,  a p-value≤0.01 and * a pvalue≤0.001 in comparison with the *L. plantarum* SH1313 (LMG P-28884).

FIG. 7 Table 4 shows the antagonistic activity of the combination of five different *Lactobacillus* strains against strains of *Salmonella* and *Escherichia coli*; +++ indicates good inhibition (zone of inhibition >5-10 mm). ++++ indicates strong inhibition (zone of inhibition >10 mm).

FIG. 8 Deposit receipt and viability statement for *Lactobacillus salivarius* CW30 (LMG P-28887).

FIG. 9 Deposit receipt and viability statement for *Lactobacillus brevis* SH111 (LMG P-28888).

FIG. 10 Deposit receipt and viability statement for *Lactobacillus plantarum* SH1313 (LMG P-28884).

FIG. 11 Deposit receipt and viability statement for *Lactobacillus plantarum* KS11 (LMG P-28885).

FIG. 12 Deposit receipt and viability statement for *Lactobacillus plantarum* Y1An734 (LMG P-28886).

FIG. 13 Carbohydrate profiling of *Lactobacillus salivarius* CW30 (LMG P-28887), *Lactobacillus brevis* SH111 (LMG P-28888), *Lactobacillus plantarum* SH1313 (LMG P-28884), *Lactobacillus plantarum* KS11 (LMG P-28885) and *Lactobacillus plantarum* Y1An734 (LMG P-28886), respectively. Scores are related to the color intensity. A positive test is indicated by a color change from purple to yellow (1-3) due to anaerobic production of acid (−=no change).

DETAILED DESCRIPTION OF THE INVENTION

In the present context and invention, the following definition apply: The term "intestinal infection and inflammation" is intended to mean gastroenteritis, an increased inflammation of the gastrointestinal tract caused by viral, bacterial or parasitic infections. It may also mean other gastrointestinal condition e.g. irritable bowel syndrome (IBS), inflammatory bowel diseases (IBD), pouchitis or post infection colitis. The term antibiotic-associated diarrhoea (AAD) is intended to mean diarrhea that develops in a person who is taking or recently took antibiotics. One of the most serious causes of AAD is infection with a bacterium, *Clostridium difficile* (CD) a Gram-positive anaerobic bacterium. Furthermore, nosocomial diarrhea infections are mainly triggered by CD but also by other enteric bacterial pathogens such as *Salmonella, Shigella, Camphylobacter*, and *Yersinia*.

The present invention provides a symbiotic composition, comprising an effective amount *Lactobacillus* bacteria chosen from the group comprising or consisting of one or more of *Lactobacillus salivarius* CW30 (LMG P-28887), *Lactobacillus brevis* SH111 (LMG P-28888), *Lactobacillus plantarum* SH1313 (LMG P-28884), *Lactobacillus plantarum* KS11 (LMG P-28885) and *Lactobacillus plantarum* Y1An734 (LMG P-28886). The bacterial strains are selected from novel lactic acid bacterial strains isolated from different plant sources. Samples from different vegetable plants, raw and after fermentation, were plated on Rogosa agar and incubated for 24-72 h at 35-42° C. in anaerobic conditions. Single clones were randomly chosen. All clones with gram positive rod shape bacteria were checked for probiotic properties such as resistance to acidic pH (pH≤3) and bile salt. The isolated bacteria were identified through carbohydrate fermentation profiling (see Table 5 in FIG. 13) and 16S rRNA sequencing. The lactic acid bacterial strains bacterial strains were further selected for ability to adhere to the intestine and inhibit the growth of gastrointestinal pathogens, but not the growth of each other. Typically, when a composition comprises more than one of these bacterial strains, the number of bacterial cells of the different bacterial strains are about equal (i.e. about the same number of bacterial cells, e.g. as determined by measuring the number of CFU or by microscopic calculation of the number of bacteria). A composition comprising one or more of these bacterial strains may be denoted a probiotic composition.

The present invention provides pharmaceutical compositions comprising at least one strain according to the invention, i.e. at least one strain selected from the group consisting of *Lactobacillus salivarius* CW30 (LMG P-28887), *Lactobacillus brevis* SH111 (LMG P-28888), *Lactobacillus plantarum* SH1313 (LMG P-28884), *Lactobacillus plantarum* KS11 (LMG P-28885) and *Lactobacillus plantarum* Y1An734 (LMG P-28886). The present invention is also directed to a culture, a composition or a product comprising one or more of said bacterial strains for use in the prevention and/or treatment of gastrointestinal condition, such as a condition caused by CD.

In the present study more than 18 different and novel lactobacilli strains have been screened and characterized regarding antimicrobial activities against 21 pathogenic CD strains. Interestingly, it turned out that these properties are strain specific and not general for all strains of a genus. A therapeutic composition of the invention comprising bacteria from all of the *Lactobacillus salivarius* CW30 (LMG P-28887), *Lactobacillus brevis* SH111 (LMG P-28888), *Lactobacillus plantarum* SH1313 (LMG P-28884), *Lactobacillus plantarum* KS11 (LMG P-28885) and *Lactobacillus plantarum* Y1An734 (LMG P-28886) strains has shown the ability to inhibit growth of all CD strains but not the growth of each other. It demonstrates the synergy exhibited between the strains of the composition of the present invention.

As is demonstrated in the experimental data provided in this document *L. plantarum* SH1313 (LMG P-28884), *L. brevis* SH111 (LMG P-28888), and *L. salivarius* CW30 (LMG P-28887) have a higher colonization ability (as demonstrated by binding to Caco-2 cells) than *L. plantarum* KS11 (LMG P-28885) and *L. plantarum* Y1An734 (LMG P-28886), although the latter still show good colonization ability. *L. plantarum* SH1313, KS11, and Y1An734 on the other hand were demonstrated to have the highest anti-inflammatory effect (as measured by potential to induce Tregs). A composition comprising *L. plantarum* SH1313, KS11, and Y1An734 may thus be particularly useful in the treatment and/or prevention of a chronic inflammatory disorder such as, but not restricted to, IBD, which includes, among other conditions, Crohn's disease and Ulcerative colitis, pouchitis or post infection colitis. *L. brevis* SH111 (LMG P-28888), and *L. salivarius* CW30 (LMG P-28887) show the strongest anti-microbial effect of the five lactobacilli strains isolated. A composition comprising *L. brevis* SH111 (LMG P-28888), and *L. salivarius* CW30 (LMG P-28887) may thus be particularly useful for use in the treatment and/or prevention of a microbial gastrointestinal infection, such as an infection caused by *Clostridium difficile, Salmonella, Escherichia coli, Campylobacter, Shigella, Yersinia, Staphylococcus, Listeria, Vibrio*, and/or *Bacillus cereus*. The gastrointestinal infection may be due to a viral infection, such as Rotavirus.

Due to inhibitory properties of the chosen lactobacilli strains on pathogenic strains of CD and/or other gut pathogens and therapeutic effect on patients with antibiotic-associated diarrhea (AAD), the present invention relates to the medical use of the symbiotic *Lactobacillus* combinations for the preparation of pharmaceutical compositions for preventing, treating, or ameliorating symptoms of a gastrointestinal condition selected from, but not limited to, AAD, gastroenteritis, acute gastroenteritis, or infectious diarrhoea. The gastrointestinal condition may be a bacterial infection caused by, but not limited to, *Clostridium difficile, Salmonella, Escherichia coli, Campylobacter, Shigella, Yersinia, Staphylococcus, Listeria, Vibrio,* or *Bacillus cereus*. The gastrointestinal condition may be due to a viral infection, such as Rotavirus associated diarrhoea, or a post infective diarrhoea.

The compositions of the present document may also be used effectively in the treatment of gastroenteritis caused by *Salmonella* or *Escherichia coli. Salmonella* spp. cause one of the most common forms of food poisoning worldwide. The experiments clearly demonstrated that the symbiotic composition of this invention strongly inhibited the growth of pathogenic strains of *Salmonella* (*S. enteritidis* and *S. typhimurium*) and *Escherichia coli*.

The present invention also relates prophylactic (preventive) use against CD infections. Patients with CD infection are usually treated with antibiotics, such as metronidazole and vancomycin. The composition of this invention has further been tested experimentally and revealed no sensitivity against metronidazole and vancomycin showing its potential to be used as a prophylactic (preventive) treatment, for example during longer periods of intake of antibiotics in order to support and/or preserve and/or restore a healthy bacterial flora of the gastrointestinal tract. It can also be used to inhibit the recurrence which is common and represent the greatest challenge associated with CD infections.

The present invention also relates treatment of infections caused by the hypervirulent CD referred to as NAP1/027. The raised incidence and virulence of CD infections have coincided with the spread of CD NAP1/027. Screening of the novel lactobacilli revealed that only few *Lactobacillus* strains had the potential to inhibit the growth of the 2 different hypervirulent CD NAP1/027 strains. These therapeutic strains are included in the symbiotic composition presented by this invention.

The present document is also directed to the use of the symbiotic composition sated in this invention for the prophylactic or therapeutic treatment of chronic inflammatory disorders such as, but not restricted to, IBD which includes, among other conditions, Crohn's disease and Ulcerative colitis, pouchitis or post infection colitis. Interaction of bacterial pathogens with the intestinal epithelial cells initiates a cascade of inflammatory processes that contribute to a gastrointestinal condition. An altered intestinal microbiota and inflammation disrupts the gut barrier function, allowing pathogens to further multiply and colonize the gut. Foxp3$^+$ Regulatory T cells (Tregs) are essential in the maintenance of immune tolerance in the gut suppressing harmful inflammatory responses. Based on our experiences, the combinations of lactobacilli have further been screened for the potential to trigger Tregs. The therapeutic composition of the invention has shown the greatest potential to trigger these anti-inflammatory cells compared to other tested combinations. It once again indicated the synergy displayed between the strains of the composition of the present invention.

The present document is also directed to the use of symbiotic composition sated in this invention for the prophylactic or therapeutic treatment of intestinal conditions associated with abdominal discomfort or pain such as, but not restricted to, irritable bowel syndrome (IBS). A role for gut microbiota and influence of stress has been suggested to be crucial for development IBS. The therapeutic composition presented in this invention has shown major success for treatment of IBS.

The composition may be administered orally. The strains of the composition of the present invention are all selected due to their unique and superior abilities to survive in the low pH of the stomach and in the high bile acid content of the small intestine, and ability to attach to colonic mucosa and to temporary colonise the large intestine. The composition may be administered as a beverage, in which case the bacterial strain(s) are suspended in a liquid. The liquid may be water, milk, a salt-sugar solution or a gruel. Alternatively, the composition may be administered as a porridge or pudding. The composition may be included in a pill, which can be swallowed by the patient.

The composition may be administered as an enema. An advantage of this route of administration is that the composition may be administered at the location in the gastrointestinal tract where it is most effective. Fecal microbiota transplant administered by enema has been used for treatment of patients. Although using enema is considered to be safe and the technique demonstrated some promising results for treating CD infections, but physicians are concerned about potential infection risks and long-term safety due to the content of the therapy which is fecal bacteria from voluntary donors. However, the therapeutic composition presented in this invention consist of *Lactobacillus* strains chosen form extensive studies which have been tested on patients with great success. A further advantage of the method is that it is performed by healthcare professionals; the patients can content with a few treatments and will be assessed regularly by care providers.

The composition may be administered as an infusion into the upper gastrointestinal tract. The composition may be administered through a medical device, such as a nasoduodenal tube. An advantage of this route of administration is that the composition may be administered at the location in the gastrointestinal tract in gastrointestinal conditions where it is most effective.

The bacterial combination may be administrated together with a pharmaceutically acceptable liquid component, but also as a powder. Preferably, distilled water or buffered aqueous media are used, which contain pharmaceutically acceptable salts and buffers. The bacterial strains may be present in a so that a total concentration of bacteria of at least $10^9$ to $10^{13}$ CFU is administered per treatment. If more than one of the bacterial strains is to be administered, typically the same amount of all different strains is administered.

The composition may further comprise a fiber component. The health benefits of dietary fiber have long been appreciated. Some of them are also known to selectively stimulate the growth and/or activity of one or a limited number of commensal bacteria in the colon, thus improving host health.

One or more pharmaceutically acceptable liquid components may be needed. Such components are well known to those skilled in the art.

The composition may further comprise a fiber component. The fiber component may be chosen from the group consisting of, but not limited to, oat fiber, wheat fiber, rye fiber, chia fiber, corn fiber, barley fiber, potato fiber, fruit fiber, vegetable fiber, cereal fiber and fiber from algae. The bacterial combination may also be suspended in a gruel, a pap, a porridge or a pudding.

In order to prepare a composition according to the present document, the bacterial strains to be included in the composition may be grown separately or in combination of one or more strains. If grown separately and more than one bacterial strain is intended to be administered, typically the different bacterial strains are mixed so that the resulting composition comprises the same amount (equal amount) of bacteria (CFU). The lactobacilli strains disclosed herein may be grown in any media commonly used for growing lactobacilli, such as Man-Rogosa-Sharpe (MRS) broth/agar and Rogosa agar. The bacteria are typically grown at a temperature of about 25 to 42° C., such as 30 to 37° C., in particular about 37° C. The bacteria may be grown in liquid culture with or without shaking or on solid media. Typically, the bacteria are grown for a time period of 24-72 hours. The time of growth will as is known to the person skilled in the art depend upon different factors, such as the temperature, the amount of bacteria inoculated, the nutrient content of the medium etc. Typically, the bacteria are grown to the stationary phase. Before the bacteria are administered to a subject in need thereof, the bacteria are typically isolated from their used growth medium by e.g. centrifuging or filtering the bacterial culture. The bacteria may be washed one or more times in e.g. a buffer or salt solution, such as in PBS (phosphate buffered saline) buffer or 0.9% NaCl. Before use, the bacteria may then be resuspended in the medium to be used for administration. The bacteria may also be freeze-dried in order to prolong their storage ability. The freeze-dried bacteria may be administered in their dry state or they may be dissolved in a liquid or liquid-containing medium before administration. It is also possible to reactivate the freeze-dried bacteria in a suitable medium for 24 h at room temperature or up to one week at 4° C. However, it should be noted that the time period and temperature for such a reactivation may vary depending on i.e. the medium used. It is also possible to use the bacterial cultures directly without separating them from their used growth medium. It is also possible to separate the bacteria from their used growth medium and administer the used growth medium instead of the bacteria themselves.

The invention will now be described in more detail in the following sections. The examples are however only illustrative and not intended to limit the scope of the present invention.

EXPERIMENTS

Assessment of interaction between lactobacilli and *Clostridium difficile*: To assess in vitro interaction between lactobacilli and *Clostridium difficile*, antagonistic activity of 18 *Lactobacillus* strains against 21 pathogenic *C. difficile* including two hyper-virulent CD NAP1/027 (also known as CD BI/NAP1/027 or CD NAP1/027) strains was determined. The CD strains belonged to different genotypes and were previously isolated from feces of hospitalized patients in Sweden, mainly at Skåne University Hospital in Malmö, with random cases of antibiotic-associated diarrhea were included. Antagonistic activity of lactobacilli was detected on agar plates as inhibition of *C. difficile* growth. The results are summarized in Table 1. *Lactobacillus* strains were cultured 48 h in Man-Rogosa-Sharpe (MRS) broth at 37° C. *C. difficile* strains were cultured 24 h in brain heart infusion (BHI) broth at 37° C. in an anaerobic environment. All bacterial cultures were centrifuged at 4° C. and pellet were suspended in 0.9% NaCl solution to prepare the concentration equal to 0.5 on the McFarland turbidity scale. 100 µl of *C. difficile* suspension was inoculated and spread onto Wilkins-Chalgren blood agar plates. 10 µl of each *lactobacillus* suspension were streaked in different lines (about 2 cm). Plates were incubated in an anaerobic environment at 37° C. for 48 h, and inhibition zones of *Lactobacillus* growth on *C. difficile* streak were investigated.

The results clearly demonstrate that *L. plantarum* strains SH1313 (LMG P-28884), KS11 (LMG P-28885) and Y1An734 (LMG P-28886), as well as *S. salivarius* CW30 (LMG P-28887) and *L. brevis* SH111 (LMG P-28888) inhibit the growth of several of the tested *C. difficile* strains. Particularly, a mixture of these five strains inhibited the growth of all tested *C. difficile* strains. In addition, *S. salivarius* CW30 (LMG P-28887) and *L. brevis* SH111 (LMG P-28888) and also *L. plantarum* KS11 (LMG P-28885) inhibited the growth of CD NAP1/027 strains. Particularly, a mixture of these five strains inhibited the growth of both of the tested CD NAP1/027 strains. Notably, other tested strains of Lactobacilli did not inhibit the growth of *C. difficile* to the same extent.

Interactions of lactobacilli and immune cells: It has been shown that direct interaction of *C. difficile* with the intestinal epithelial cells initiates a cascade of inflammatory processes that contribute to intestinal diseases such as diarrhea and pseudomembranous colitis. An altered intestinal microbiota composition and inflammation disrupts the gut barrier function, allowing *C. difficile* to further multiply and colonize the gut. Foxp3 expressing $CD4^+$ T cells (Regulatory T cells; Tregs) are essential in the maintenance of immune tolerance in the gut suppressing harmful inflammatory responses. Based on previous experiences, we have isolated intestinal lymphoid tissues (Peyer's patches and mesenteric lymph nodes) from mice. They were pooled and single cells suspensions of immune cells were provided in vitro. The cells were then co-incubated with five different lactobacilli; *L. plantarum* SH1313 (LMG P-28884), *L. salivarius* CW30 (LMG P-28887), *L. brevis* SH111 (LMG P-28888), *L. plantarum* KS11 (LMG P-28885), and *L. plantarum* Y1An734 (LMG P-28886) in single or combinations together. A total of $1\times10^6$ of immune cells was seeded/well in a 96-well plate (in the RPMI 1640 cell culture medium). $1\times10^7$ CFU/ml (100 µl) of bacteria (suspended in RPMI 1640) were added to the cells and the co-culture was incubated for 20 h (37° C., humidified atmosphere with 5% $CO_2$). At the next day, the cells were washed and analysed for prevalence of Tregs using flow cytometry. Tregs were detected expressing the receptor CD4, transcription factor (forkhead box P3; Foxp3), and intracellular cytokine IL-10. The bacteria were used either in single form or in combinations of two, three, four of five strains. The combinations contained equal amounts of each strains (added at the same day of experiment), all to a final concentration of $1\times10^7$ CFU/ml. Control samples contained cell culture medium only. The results are shown in FIG. 1. The data represent the frequency of $CD4^+Foxp3^+$ T cells in percent.

It was clearly evident from the results that only selected single strains of *L. plantarum* (SH1313, KS11, or Y1An734), have the potential to induce an anti inflammatory profile and activate Tregs among the cells from freshly isolated intestinal lymphoid tissues. *L. salivarius* CW30, *L. brevis* SH111 can trigger Tregs only in combination with carefully selected strains of *L. plantarum*. The results also demonstrated that the *L. plantarum* SH1313, *L. plantarum* KS11, *L. plantarum* Y1An734, *L. salivarius* CW30, and *L. brevis* SH111 work synergistically to activate and increase Tregs. The most significant and profound anti-inflammatory effect achieves by using a combination of all five strains.

Using the same assay, we have further compared the potential of different lactobacilli to induce Tregs. We have used *L. plantarum* SH1313 (LMG P-28884), *L. salivarius* CW30 (LMG P-28887), *L. brevis* SH111 (LMG P-28888), *L. plantarum* KS11 (LMG P-28885), *L. plantarum* Y1An734 (LMG P-28886) and four lactobacilli strains isolated from different commercially available food products; *L. paracasei* CNCM I-1518 (Actimel), *L. plantarum* DSM 9843 (ProViva), *L. acidophilus* DSM 13241 (Arta A-fil) and *L. rhamnosus* ATCC 53103 (Valio yoghurt). $1 \times 10^7$ CFU/ml (100 μl) of each strain were co-cultured with immune cells for 20 h at 37° C. The results are shown in FIG. 2. The data represent the frequency of CD4$^+$Foxp3$^+$ T cells in percent.

The results revealed that *L. plantarum* (SH1313, KS11, and Y1An734) have significantly stronger potential to induce Tregs than other strains including the *L. paracasei* CNCM I-1518, *L. plantarum* DSM 9843, *L. acidophilus* DSM 13241 and *L. rhamnosus* ATCC 53103, i.e. that these *L. plantarum* strains (*L. plantarum* (SH1313, KS11, and Y1An734)) have a pronounced anti-inflammatory effect.

Statistical evaluations were all performed using StatView and the data were evaluated using nonparametric Mann-Whitney test.

Inter-species inhibition of five different *Lactobacillus* strains: There are increasing evidence showing that certain mixtures of *Lactobacillus* species have more beneficial effects than their component strains. The various synergistic or additive effects in vivo has been suggested to be influenced by possible mutual inhibition by the component strains. We investigated whether the five different lactobacilli; *L. plantarum* SH1313 (LMG P-28884), *L. salivarius* CW30 (LMG P-28887), *L. brevis* SH111 (LMG P-28888), *L. plantarum* KS11 (LMG P-28885), and *L. plantarum* Y1An734 (LMG P-28886) may inhibit the growth of the others in vitro. A cross-streak assay was used for this purpose. Each strain was streaked onto MRS agar using a 1 ml loop (3 parallel lines). After the lines had dried, other strains were streaked perpendicular to these strains creating 3 potential zones of inhibition for each combination of strains. If the tester strain hindered the growth of the second-streaked strain, it implicated an inhibition. The results are shown in Table 2.

The results clearly revealed that *L. salivarius* CW30, and *L. brevis* SH111, have very little, and the *L. plantarum* SH1313, *L. plantarum* KS11, *L. plantarum* Y1An734, have no ability to inhibit the growth of the other selected bacterial strains. Despite the fact that the proposed multi-strain lactobacilli preparation (consisting of *L. salivarius* CW30, and *L. brevis* SH111, *L. plantarum* SH1313, *L. plantarum* KS11, and *L. plantarum* Y1An734) can maintain inhibition of a range of pathogenic *C. difficile*, there is no inhibition between the component strains influencing the therapeutic efficacy of the bacterial mixture.

Antibiotic susceptibility of *Lactobacillus* strains: The antibiotic susceptibilities of lactobacilli have shown to be species- and strain-dependent. Therefore, the antibiotic susceptibility of the five different lactobacilli; *L. plantarum* SH1313 (LMG P-28884), *L. salivarius* CW30 (LMG P-28887), *L. brevis* SH111 (LMG P-28888), *L. plantarum* KS11 (LMG P-28885), and *L. plantarum* Y1An734 (LMG P-28886) were examined using disk diffusion test. Rogosa Agar plates were inoculated with bacteria from freshly prepared cultures of *Lactobacillus* strains. Disk diffusion tests were carried out for erythromycin (15 μg disk), vancomycin (30 μg disk), and metronidazole (5 μg disk). The results are shown in Table 3. "S", stands for sensitive and "R", stands for resistant.

The antibiotic profiling data reveals that *L. salivarius* CW30, and *L. brevis* SH111, *L. plantarum* SH1313, *L. plantarum* KS11, and *L. plantarum* Y1An734 are all sensitive to erythromycin, which is a type of medicine known as a macrolide antibiotic, and none of the strains is sensitive to vancomycin or metronidazole.

Adhesion of lactobacilli strains to human enterocyte-like Caco-2 cells: The adhesion of lactobacilli strains to the intestinal mucosa is one of the appropriate properties for their colonization in the intestinal tract, where they compete with other bacteria. The human intestinal cell line Caco-2 (from colonic adenocarcinoma) is a well characterized cellular model which develops characteristics of mature enterocytes with functional brush-border microvilli when fully differentiated. The Caco-2 cell line has been extensively used to study bacterial adhesion and invasion.

In the present study, the adhesion of the various *Lactobacillus* strains to Caco-2 cells was compared. Caco-2 cells were grown in 100-mm plastic Petri dishes. Cells were seeded at approximately $5 \times 10^5$ in a 35-mm dish and used two weeks after confluence (fully differentiated cells). Bacterial cells ($5 \times 10^8$) were added to washed cell monolayers and incubated for 1 h at 37° C. We have used *L. plantarum* SH1313 (LMG P-28884), *L. salivarius* CW30 (LMG P-28887), *L. brevis* SH111 (LMG P-28888), *L. plantarum* KS11 (LMG P-28885), *L. plantarum* Y1An734 (LMG P-28886) and four lactobacilli strains isolated from different commercially available food products; *L. paracasei* CNCM I-1518, *L. plantarum* DSM 9843, *L. acidophilus* DSM 13241, and *L. rhamnosus* ATCC 53103.

All monolayers were then washed 3 times with PBS to release unbound bacteria and stained with Giemsa stain solution. Dishes were then washed, dried for 1 h and examined microscopically (magnification ×100) under oil immersion. The *Lactobacillus* strains in 20 randomly selected microscopic fields were counted and averaged.

As indicated in FIG. 6, there were significant variations in adherence of different lactobacilli strains to the Caco-2 cells, indicating that adhesive properties are not a universal feature of lactobacilli. *L. plantarum* SH1313 (LMG P-28884), *L. brevis* SH111 (LMG P-28888), and *L. salivarius* CW30 (LMG P-28887) showed strongest efficiency of adhesion to Caco-2 cells. Although the adhesion properties of *L. plantarum* KS11 (LMG P-28885), *L. plantarum* Y1An734 (LMG P-28886), and *L. paracasei* CNCM I-1518 are a bit weaker their adherence to Caco-2 cells still seems more prominent than the adhesion properties of *L. plantarum* DSM 9843, *L. acidophilus* DSM 13241, and *L. rhamnosus* ATCC 53103.

Antagonistic activity of a combination of *Lactobacillus* strains against strains of *Salmonella* and *Escherichia coli*: We have further evaluated the ability of the combination of five lactobacilli; *L. plantarum* SH1313 (LMG P-28884), *L. salivarius* CW30 (LMG P-28887), *L. brevis* SH111 (LMG P-28888), *L. plantarum* KS11 (LMG P-28885), and *L. plantarum* Y1An734 (LMG P-28886) to inhibit the in vitro growth of *Salmonella enteritidis, Salmonella typhimurium*, and *Escherichia coli*. *Lactobacillus* strains were cultured 48 h in Man-Rogosa-Sharpe (MRS) broth at 37° C. *Salmonella* and *E. coli* strains were cultured 24 h in brain heart infusion (BHI) broth at 37° C. All bacterial cultures were centrifuged at 4° C. and the pellets were suspended in 0.9% NaCl solution to prepare the concentration equal to 0.5 on the McFarland turbidity scale. 100 μl cell suspensions of *Salmonella* or *E. coli* strains were inoculated and spread onto Wilkins-Chalgren blood agar plates. A mixture containing equal amounts of each five *Lactobacillus* strains (added at the same day of experiment), were prepared to a final concentration of 1×10⁷ CFU/ml. 10 µl of *Lactobacillus* suspension were streaked in different lines (about 2 cm). Plates were incubated for 48 h at 37° C. (with 5% $CO_2$). The growth inhibition zones were then measured.

As indicated in the Table 4, the results clearly demonstrate that a combination of *L. salivarius* CW30, and *L. brevis* SH111, *L. plantarum* SH1313, *L. plantarum* KS11, and *L. plantarum* Y1An734 is able to strongly inhibit growth of the *Salmonella enteritidis, Salmonella typhimurium*, and *Escherichia coli*. The data further demonstrate the antimicrobial potential of the lactobacilli mixture against gastrointestinal pathogenic bacteria.

Clinical Cases

The present invention is demonstrated by the following examples of clinical trials which were performed at the Department of Infectious Diseases, Skåne University Hospital in Malmö, Sweden, (during 2013-2014). The implicated examples, materials and procedures are to be understood broadly with the scope and spirit of the invention as set forth herein.

Case 1: *Clostridium difficile* infection is a complication commonly associated with antibiotic therapy in hospitalized patients. A 70 years old female patient with ongoing anal cancer and stoma surgery receives several courses of antibiotics due to wound problems. She showed recurrent *C. difficile* colitis during one year and were treated several times with metronidazole and then vancomycin with a de-escalation strategy under six weeks. Once more, she developed recurrent *C. difficile* infection (CDI).

Method: A combination of five lactobacilli; *L. plantarum* SH1313 (LMG P-28884), *L. salivarius* CW30 (LMG P-28887), *L. brevis* SH111 (LMG P-28888), *L. plantarum* KS11 (LMG P-28885), and *L. plantarum* Y1An734 (LMG P-28886) were provided (equal amounts of each strain). 1×10¹² CFU were combined with a sterile fiber-rich gruel. The composition was then mixed to an enema solution and a colonic infusion was performed by a rectal tube. The treatment was repeated five times with an interval of 3-5 days.

Result: The patient was clinically and bacteriological cured after 3 months and showed no sign of recurrent infection up to one year after the last treatment.

Case 2: A 75 years old male patient with multiple diseases. He showed recurrent *C. difficile* colitis after long-term treatment with Dalacin, containing the antibiotic called clindamycin hydrochloride, the year before. He received two courses of metronidazole, followed by 10 days of vancomycin treatment. After six weeks under de-escalation strategy, he showed recurrent CDI. He received a fecal microbiota transplantation containing feces from healthy donors prepared by the clinical investigators at the hospital. After new course of the antibiotic treatment he developed recurrent CDI once more.

Method: A composition of five lactobacilli was provided as described above and the enema solution was infused. The treatment was repeated three times with an interval of 7 days.

Result: The patient was clinical cured after a few days and showed no sign of recurrent infection up to one year after the last treatment.

Case 3: A 55 years old female patient showed recurrent *C. difficile* colitis after long-term antibiotic treatments. She received two courses of metronidazole, followed by 10 days of vancomycin treatment. After six weeks under de-escalation strategy, she showed recurrent CDI.

Method: A composition of five lactobacilli was provided as described above and the enema solution was infused. The treatment was repeated three times with an interval of 7 days.

Result: The patient was clinical cured after a few days and showed no sign of recurrent infection up to one year after the last treatment.

Case 4: A young man, 20 years old, developed irritable bowel syndrome (IBS) after earlier gastroenteritis. He received fecal microbiota transplantation containing feces from healthy donors (prepared by the clinical investigators at the hospital) at two occasions with no sign of improvement of his condition.

Method: A composition of five lactobacilli was provided as described above and the enema solution was infused. The treatment was repeated three times with an interval of 7 days.

Result: The patient showed significant improvement in symptomatology of IBS. He has not shown any signs of clinical deterioration up to one year after the last treatment. The results from the clinical investigations demonstrate that a bacterial composition consisting of *L. plantarum* SH1313 (LMG P-28884), *L. salivarius* CW30 (LMG P-28887), *L. brevis* SH111 (LMG P-28888), *L. plantarum* KS11 (LMG P-28885), and *L. plantarum* Y1An734 (LMG P-28886), is effective and relatively safe for treatment of patients suffering from severe gastrointestinal conditions

SPECIFIC EMBODIMENTS

1. Composition for use in the treatment and/or prevention of a gastrointestinal condition, comprising *L. salivarius* CW30 (LMG P-28887).

2. Composition for use in the treatment and/or prevention of a gastrointestinal condition, comprising *L. salivarius* CW30 (LMG P-28887) and *L. plantarum* Y1An734 (LMG P-28886).

3. Composition for use in the treatment and/or prevention of a gastrointestinal condition, comprising *L. salivarius* CW30 (LMG P-28887), and *L. plantarum* SH1313 (LMG P-28884).

4. Composition for use in the treatment and/or prevention of a gastrointestinal condition, comprising *L. salivarius* CW30 (LMG P-28887) and *L. plantarum* KS11 (LMG P-28885).

5. Composition for use in the treatment and/or prevention of a gastrointestinal condition, comprising *L. salivarius* CW30 (LMG P-28887) and *L. brevis* SH111 (LMG P-28888).

6. Composition for use in the treatment and/or prevention of a gastrointestinal condition, comprising *L. salivarius* CW30 (LMG P-28887), *L. plantarum* Y1An734 (LMG P-28886) and *L. plantarum* SH313 (LMG-28884).

7. Composition for use in the treatment and/or prevention of a gastrointestinal condition, comprising *L. salivarius* CW30 (LMG P-28887), *L. plantarum* Y1An734 (LMG P-28886) and *L. plantarum* KS11 (LMG P-28885.

8. Composition for use in the treatment and/or prevention of a gastrointestinal condition, comprising *L. salivarius* CW30 (LMG P-28887), *L. plantarum* Y1An734 (LMG P-28886), and *L. brevis* SH111 (LMG P-28888).

9. Composition for use in the treatment and/or prevention of a gastrointestinal condition, comprising *L. salivarius* CW30 (LMG P-28887), *L. plantarum* SH1313 (LMG P-28884) and *L. plantarum* KS11 (LMG P-28885).

10. Composition for use in the treatment and/or prevention of a gastrointestinal condition, comprising *L. salivarius*

CW30 (LMG P-28887), *L. plantarum* SH1313 (LMG P-28884) and *L. brevis* SH111 (LMG P-28888).

11. Composition for use in the treatment and/or prevention of a gastrointestinal condition, comprising *L. salivarius* CW30 (LMG P-28887), *L. plantarum* KS11 (LMG P-28885) and *L. brevis* SH111 (LMG P-28888).

12. Composition for use in the treatment and/or prevention of a gastrointestinal condition, comprising *L. salivarius* CW30 (LMG P-28887), *L. plantarum* KS11 (LMG P-28885), *L. brevis* SH111 (LMG P-28888).

13. Composition for use in the treatment and/or prevention of a gastrointestinal condition, comprising *L. salivarius* CW30 (LMG P-28887), *L. plantarum* Y1An734 (LMG P-28886), *L. plantarum* SH1313 (LMG P-28884) and *L. plantarum* KS11 (LMG P-28885).

14. Composition for use in the treatment and/or prevention of a gastrointestinal condition, comprising *L. salivarius* CW30 (LMG P-28887), *L. plantarum* Y1An734 (LMG P-28886), *L. plantarum* KS11 (LMG P-28885) and *L. brevis* SH111 (LMG P-28888).

15. Composition for use in the treatment and/or prevention of a gastrointestinal condition, comprising *L. salivarius* CW30 (LMG P-28887), *L. plantarum* SH1313 (LMG P-28884), *L. plantarum* KS11 (LMG P-28885) and *L. brevis* SH111 (LMG P-28888).

16. Composition for use in the treatment and/or prevention of a gastrointestinal condition, comprising *L. salivarius* CW30 (LMG P-28887), *L. plantarum* Y1An734 (LMG P-28886), *L. plantarum* SH1313 (LMG P-28884), *L. plantarum* KS11 (LMG P-28885), and *L. brevis* SH111 (LMG P-28888).

17. Composition for use in the treatment and/or prevention of a gastrointestinal condition, comprising *L. plantarum* Y1An734 (LMG P-28886).

18. Composition for use in the treatment and/or prevention of a gastrointestinal condition, comprising *L. plantarum* Y1An734 (LMG P-28886) and *L. plantarum* SH1313 (LMG P-28884).

19. Composition for use in the treatment and/or prevention of a gastrointestinal condition, comprising *L. plantarum* Y1An734 (LMG P-28886) and *L. plantarum* KS11 (LMG P-28885).

20. Composition for use in the treatment and/or prevention of a gastrointestinal condition, comprising *L. salivarius* CW30 (LMG P-28887) and *L. brevis* SH111 (LMG P-28888).

21. Composition for use in the treatment and/or prevention of a gastrointestinal condition, comprising *L. plantarum* Y1An734 (LMG P-28886), *L. plantarum* SH1313 (LMG P-28884) and *L. plantarum* KS11 (LMG P-28885).

22. Composition for use in the treatment and/or prevention of a gastrointestinal condition, comprising *L. plantarum* Y1An734 (LMG P-28886), *L. plantarum* SH1313 (LMG P-28884) and *L. brevis* SH111 (LMG P-28888).

23. Composition for use in the treatment and/or prevention of a gastrointestinal condition, comprising *L. plantarum* Y1An734 (LMG P-28886), *L. plantarum* KS11 (LMG P-28885), *L. brevis* SH111 (LMG P-28888).

24. Composition for use in the treatment and/or prevention of a gastrointestinal condition, comprising *L. plantarum* Y1An734 (LMG P-28886), *L. plantarum* SH1313 (LMG P-28884), *L. plantarum* KS11 (LMG P-28885) and *L. brevis* SH111 (LMG P-28888).

25. Composition for use in the treatment and/or prevention of a gastrointestinal condition, comprising *L. plantarum* SH1313 (LMG P-28884).

26. Composition for use in the treatment and/or prevention of a gastrointestinal condition, comprising *L. plantarum* SH1313 (LMG P-28884) and *L. plantarum* KS11 (LMG P-28885).

27. Composition for use in the treatment and/or prevention of a gastrointestinal condition, comprising *L. plantarum* SH1313 (LMG P-28884) and *L. brevis* SH111 (LMG P-28888).

28. Composition for use in the treatment and/or prevention of a gastrointestinal condition, comprising *L. plantarum* SH1313 (LMG P-28884), *L. plantarum* KS11 (LMG P-28885) and *L. brevis* SH111 (LMG P-28888).

29. Composition for use in the treatment and/or prevention of a gastrointestinal condition, comprising *L. plantarum* KS11 (LMG P-28885).

30. Composition for use in the treatment and/or prevention of a gastrointestinal condition, comprising *L. plantarum* KS11 (LMG P-28885) and *L. brevis* SH111 (LMG P-28888).

31. Composition for use in the treatment and/or prevention of a gastrointestinal condition, comprising *L. brevis* SH111 (LMG P-28888).

32. Composition for use according to any one of the previous embodiments, wherein the gastrointestinal condition is a diarrhoea, antibiotic-associated diarrhoea (AAD), gastroenteritis, acute gastroenteritis and infectious diarrhoea.

33. Composition for use according to any one of the previous embodiments, wherein the gastrointestinal condition is a bacterial infection by *Clostridium difficile*, *Salmonella* or *Escherichia coli*.

34. Composition for use according to any one of the previous embodiments, wherein the gastrointestinal condition is an infection by *Clostridium difficile* NAP1/027.

35. Composition for use according to any one embodiments 1 to 32, wherein the gastrointestinal condition is irritable bowel syndrome (IBS) or inflammatory bowel disease (IBD).

36. Composition for use according to any one of the previous embodiments, wherein the composition is administered orally.

37. Composition for use according to any one of the previous embodiments, wherein the composition is administered as an enema.

38. Composition for use according to any one of the previous embodiments, wherein the composition is administered as an infusion into the upper gastrointestinal tract.

39. Composition for use according to any one of the previous embodiments, wherein the total amount of *Lactobacillus* is $10^9$ to $10^{13}$ CFU per treatment and the treatment is repeated once a week for at least two times.

40. Composition for use according to any one of the previous embodiments, wherein the composition is a freeze-dried.

41. Composition for use according to embodiment 40, wherein the composition further comprises a fiber component.

42. Composition for use according to embodiment 41, wherein the fiber component is chosen from the group consisting of oat fiber, wheat fiber, rye fiber, chia fiber, corn fiber, barley fiber, potato fiber, fruit fiber, vegetable fiber, cereal fiber and fiber from algae.

43. Composition for use according to any one of embodiments 40 to 42, wherein the bacteria are suspended in a gruel, a pap, a porridge or a pudding.

44. Composition for use according to embodiment 43, wherein the gruel is oat gruel.

45. An enema comprising a composition according to any one of the preceding embodiments.

46. An isolated strain of *L. salivarius* CW30 (LMG P-28887).

47. An isolated strain of *L. plantarum* Y1An734 (LMG P-28886).

48. An isolated strain of *L. plantarum* SH1313 (LMG P-28884).

49. An isolated strain of *L. plantarum* KS11 (LMG P-28885).

50. An isolated strain of *L. brevis* SH111 (LMG P-28888).

51. An isolated strain of *L. salivarius* CW30 (LMG P-28887) for use in the treatment and/or prevention of an infection by *Clostridium difficile* NAP1/027.

52. An isolated strain according to anyone of embodiments 47 to 50 for use in the treatment and/or prevention of an infection by *Clostridium difficile* NAP1/027.

53. Method of treatment and/or prevention of a gastrointestinal condition by administering a composition according to anyone of embodiments 1 to 44 or an enema according to embodiment 45 or an isolated strain according to anyone of embodiments 46 to 50.

54. Method of treatment and/or prevention according to embodiment 53, wherein the gastrointestinal condition is a diarrhoea, antibiotic-associated diarrhoea (AAD), gastroenteritis, acute gastroenteritis and infectious diarrhoea.

55. Method of treatment and/or prevention according to embodiment 53 or 54, wherein the gastrointestinal condition is a bacterial infection by *Clostridium difficile*, *Salmonella* or *Escherichia coli*.

56. Method of treatment and/or prevention according to any one of embodiment 53 to 55, wherein the gastrointestinal condition is an infection by *Clostridium difficile* NAP1/027.

57. Method of treatment and/or prevention according to any one of embodiment 53 to 56, wherein the gastrointestinal condition is irritable bowel syndrome (IBS) or inflammatory bowel disease (IBD).

58. Method of treatment and/or prevention according to any one of embodiment 53 to 57, wherein the composition is administered orally.

59. Method of treatment and/or prevention according to any one of embodiment 53 to 58, wherein the composition is administered as an enema.

60. Method of treatment and/or prevention according to any one of embodiment 53 to 59, wherein the composition is administered as an infusion into the upper gastrointestinal tract.

61. Method of treatment and/or prevention according to any one of embodiment 53 to 60, wherein the total amount of *Lactobacillus* is $10^9$ to $10^{13}$ CFU per treatment and the treatment is repeated once a week for at least two times.

62. Use of a composition according to anyone of embodiments 1 to 44 or an enema according to embodiment 45 or an isolated strain according to anyone of embodiments 46 to 50 in the treatment and/or prevention of a gastrointestinal condition.

63. Use according to embodiment 62, wherein the gastrointestinal condition is a diarrhoea, antibiotic-associated diarrhoea (AAD), gastroenteritis, acute gastroenteritis and infectious diarrhoea.

64. Use according to embodiment 62 or 63, wherein the gastrointestinal condition is a bacterial infection by *Clostridium difficile*, *Salmonella* or *Escherichia coli*.

65. Use according to any one of embodiment 62 to 64, wherein the gastrointestinal condition is an infection by *Clostridium difficile* NAP1/027.

66. Use according to any one of embodiment 62 to 64, wherein the gastrointestinal condition is irritable bowel syndrome (IBS) or inflammatory bowel disease (IBD).

67. Use according to any one of embodiment 62 to 66, wherein the composition is administered orally.

68. Use according to any one of embodiment 62 to 66, wherein the composition is administered as an enema.

69. Use according to any one of embodiment 62 to 68, wherein the composition is administered as an infusion into the upper gastrointestinal tract.

70. Use according to any one of embodiment 62 to 69, wherein the total amount of *Lactobacillus* is $10^9$ to $10^{13}$ CFU per treatment and the treatment is repeated once a week for at least two times.

71. Use of an isolated strain of *L. salivarius* CW30 (LMG P-28887) in the treatment and/or prevention of an infection by *Clostridium difficile* NAP1/027.

72. Use of an isolated strain according to anyone of embodiments 47 to 50 for the treatment and/or prevention of an infection by *Clostridium difficile* NAP1/027.

The invention claimed is:

1. A method for the treatment and/or prevention of irritable bowel syndrome (IBS), inflammatory bowel disease (IBD), diarrhoea, antibiotic-associated diarrhoea (AAD), infectious diarrhoea, or a gastrointestinal infection caused by *Clostridium difficile*, *Salmonella* or *Escherichia coli*, said method comprising the step of administering a composition comprising a mixture of two or more *Lactobacillus* strains including a first strain selected from *L. plantarum* Y1An734 (LMG P-28886), *L. plantarum* SH1313 (LMG P-28884) or *L. plantarum* KS11 (LMG P-28885) and one or more second strains distinct from the first strain and chosen from the group consisting of *L. salivarius* CW30 (LMG P-28887), *L. plantarum* Y1An734 (LMG P-28886), *L. plantarum* SH1313 (LMG P-28884), *L. plantarum* KS11 (LMG P-28885), and *L. brevis* SH111 (LMG P-28888), wherein the strains are in an effective amount to treat a *C. difficile* gastrointestinal infection.

2. The method according to claim 1, wherein the composition comprises as a second strain *L. salivarius* CW30 (LMG P-28887).

3. The method according to claim 1, wherein the composition comprises *L. salivarius* CW30 (LMG P-28887), *L. brevis* SH111 (LMG P-28888), *L. plantarum* Y1 An734 (LMG P-28886), *L. plantarum* SH1313 (LMG P-28884), and *L. plantarum* KS11 (LMG P-28885).

4. The method according to claim 1, wherein diarrhoea, antibiotic-associated diarrhoea (AAD), or infectious diarrhea is treated or prevented.

5. The method according to claim 1, wherein a bacterial infection by *Clostridium difficile* is treated or prevented.

6. The method according to claim 5, wherein an infection by *Clostridium difficile* NAP 1/027 is treated or prevented.

7. The method according to claim 1, wherein irritable bowel syndrome (IBS) or inflammatory bowel disease (IBD) is treated or prevented.

8. The method according to claim 1, wherein the composition is administered orally or as an enema or as an infusion into the upper gastrointestinal tract.

9. The method according to claim 1, wherein the total amount of *Lactobacillus* is $10^9$ to $10^{13}$ CFU per treatment.

10. The method according to claim 1, wherein the composition is freeze-dried.

11. The method according to claim 1, wherein the composition further comprises a fiber component.

12. The method according to claim 11, wherein the fiber component is chosen from the group consisting of oat fiber, wheat fiber, rye fiber, chia fiber, corn fiber, barley fiber, potato fiber, fruit fiber, vegetable fiber, cereal fiber and fiber from algae.

13. The method according to claim 11, wherein the bacteria are suspended in a gruel, a pap, a porridge or a pudding.

14. The method according to claim 13, wherein the gruel is oat gruel.

* * * * *